US011422832B2

(12) United States Patent
Ganjam

(10) Patent No.: US 11,422,832 B2
(45) Date of Patent: Aug. 23, 2022

(54) MOLECULAR STATE MACHINES USING HDR TEMPLATE INSERTION

(71) Applicant: MICROSOFT TECHNOLOGY LICENSING, LLC, Redmond, WA (US)

(72) Inventor: Kris K. Ganjam, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 266 days.

(21) Appl. No.: 16/450,641

(22) Filed: Jun. 24, 2019

(65) Prior Publication Data

US 2019/0332396 A1 Oct. 31, 2019

Related U.S. Application Data

(62) Division of application No. 15/626,020, filed on Jun. 16, 2017, now abandoned.

(60) Provisional application No. 62/487,671, filed on Apr. 20, 2017, provisional application No. 62/399,190, filed on Sep. 23, 2016, provisional application No. 62/357,828, filed on Jul. 1, 2016.

(51) Int. Cl.

| | |
|---|---|
| ***G06F 9/448*** | (2018.01) |
| ***C12Q 1/6897*** | (2018.01) |
| ***C12N 15/90*** | (2006.01) |
| ***G06N 3/12*** | (2006.01) |
| ***C12Q 1/6869*** | (2018.01) |
| ***C12N 15/10*** | (2006.01) |
| ***C12N 15/63*** | (2006.01) |

(52) U.S. Cl.

CPC ......... *G06F 9/4498* (2018.02); *C12N 15/102* (2013.01); *C12N 15/63* (2013.01); *C12N 15/902* (2013.01); *C12Q 1/6869* (2013.01); *C12Q 1/6897* (2013.01); *G06N 3/123* (2013.01); *C12Q 2563/179* (2013.01)

(58) Field of Classification Search

None

See application file for complete search history.

(56) References Cited

U.S. PATENT DOCUMENTS

| | | | |
|---|---|---|---|
| 9,957,526 | B2 | 5/2018 | Holmes et al. |
| 2010/0047805 | A1 | 2/2010 | Wang |
| 2014/0273231 | A1 | 9/2014 | Zhang et al. |
| 2015/0376650 | A1 | 12/2015 | Auerbach et al. |
| 2016/0024524 | A1 | 1/2016 | Joung et al. |
| 2016/0040155 | A1 | 2/2016 | Maizels et al. |
| 2016/0053274 | A1 | 2/2016 | D'halluin |
| 2016/0317677 | A1 | 11/2016 | Bhatia et al. |
| 2017/0211099 | A1 | 7/2017 | Auerbach et al. |
| 2017/0369870 | A1* | 12/2017 | Gill ..................... C12N 15/102 |
| 2019/0119701 | A1 | 4/2019 | Liang et al. |
| 2020/0332317 | A1 | 10/2020 | Ganjam |

FOREIGN PATENT DOCUMENTS

| | | | |
|---|---|---|---|
| AU | 2017257225 | A1 | 11/2018 |
| CA | 2963080 | A1 | 4/2016 |
| CN | 1628174 | A | 6/2005 |
| CN | 101889088 | A | 11/2010 |
| CN | 105473773 | A | 4/2016 |
| CN | 105492611 | A | 4/2016 |
| CN | 105602993 | A | 5/2016 |
| CN | 105683379 | A | 6/2016 |
| CN | 106795521 | A | 5/2017 |
| CN | 109415724 | A | 3/2019 |
| CN | 109415725 | A | 3/2019 |
| CN | 109415726 | A | 3/2019 |
| CN | 109477130 | A | 3/2019 |
| CN | 111344403 | A | 6/2020 |
| EP | 2313515 | A1 | 4/2011 |
| EP | 3597748 | B1 | 4/2021 |
| WO | 2015116969 | A2 | 8/2015 |
| WO | 2016028682 | A1 | 2/2016 |

OTHER PUBLICATIONS

"Office Action Issued in European Patent Application No. 17742885.1", dated Feb. 20, 2020, 7 Pages.

"Final Office Action Issued in U.S. Appl. No. 15/623,925", dated Nov. 25, 2019, 12 Pages.

"Final Office Action Issued in U.S. Appl. No. 15/626,021", dated Nov. 22, 2019, 9 Pages.

"Final Office Action Issued in U.S. Appl. No. 15/625,998", dated Dec. 6, 2019, 15 Pages.

"Search Report Issued in European patent Application No. 19185657.4", dated Dec. 9, 2019, 8 Pages.

(Continued)

*Primary Examiner* — G Steven Vanni

(74) *Attorney, Agent, or Firm* — Benjamin A. Keim; Newport IP. LLC

(57) ABSTRACT

A molecular state machine is implemented in a cell by designing the cell to use specific homology directed repair ("HDR") templates for repairing double strand breaks in polynucleotides based on a current "state" of the cell. The state may be established by the presence of a molecule in the cell or by the availability of specific cut sites in the polynucleotides of the cell. Different HDR templates or different nucleases may be available for performing HDR based on the state. When the state is changed, the same signal or event will result in a different HDR template being incorporated into the existing polynucleotides of the cell. Signals that are internal or external to the cell may be used to change the state of the cell. The cell may create a log of molecular events, store binary data, or perform other synthetic biology/molecular computing functions based on state.

13 Claims, 9 Drawing Sheets

Specification includes a Sequence Listing.

(56) References Cited

OTHER PUBLICATIONS

"Non Final Office Action Issued in U.S. Appl. No. 15/625,998", dated Jul. 18, 2019, 27 Pages.
Andrianantoandro, et al., "Synthetic Biology: New Engineering Rules for an Emerging Discipline", In Journal of Molecular Systems Biology, EMBO and Nature Publishing Group, May 1, 2006, pp. 1-14.
Schmidt, et al., "Applications of CRISPR-Cas for Synthetic Biology and Genetic Recording", In Journal of Current Opinion in System Biology, vol. 5, Oct. 2017, pp. 9-15.
Sheth, et al., "DNA-based Memory Devices for Recording Cellular Events", In Journal of Nature Reviews Genetics, Sep. 20, 2018, 30 Pages.
Wikipedia, "Homology Directed Repair", Retrieved From: https://en.wikipedia.org/wiki/Homology_directed_repair, Jul. 15, 2019, 4 Pages.
"Non Final Office Action Issued in U.S. Appl. No. 15/626,021", dated Jul. 12, 2019, 10 Pages.
"Non-Final Office Action Issued in U.S. Appl. No. 15/623,925", dated May 8, 2019, 12 Pages.
"Office Action Issued in European Patent Application No. 17736842.0", dated Aug. 18, 2020, 5 Pages.
"Extended European Search Report Issued in European Patent Application No. 19185656.6", dated Mar. 13, 2020, 8 Pages.
"Non Final Office Action Issued in U.S. Appl. No. 15/625,998", dated Apr. 16, 2020, 07 Pages.
"Office Action Issued in European Patent Application No. 17736842.0", dated May 11, 2020, 3 Pages.
"First Office Action and Search Report Issued in Chinese Patent Application No. 201780041175.9", dated Aug. 26, 2021, 11 Pages.
"First Office Action and Search Report Issued in Chinese Patent Application No. 201780041255.4", dated Aug. 16, 2021, 14 Pages.
"First Office Action and Search Report Issued in Chinese Patent Application No. 201780041484.6", dated Sep. 2, 2021, 14 Pages.
"First Office Action and Search Report Issued in Chinese Patent Application No. 201780041514.3", dated Aug. 30, 2021, 21 Pages.
Chien, et al., "Multiplexed bioluminescence-mediated tracking of DNA double-strand break repairs in vitro and in vivo", In Journal of Nature Protocols, Jun. 23, 2021, 21 Pages.
Dan, et al., "The Role of BRCA1 in DNA DSB Repair Pathway", In Chinese Journal of Biochemistry and Molecular Biology, vol. 31, Issue 1, Jan. 20, 2015, pp. 28-33.
Ding, et al., "Application of real-time fluorescent quantitative PCR and experimental optimizing", In Journal of Dalian Medical University, vol. 29, Issue 4, Aug. 15, 2007, pp. 404-407.
Lan, et al., "Homologous recombination and gene targeting in Vertebrate Cells", Published in Letters in Biotechnology, vol. 17, Issue 1, Mar. 30, 2006, pp. 88-91.
Lun-Hao, et al., "The principle and applications of binary expression systems in *Drosophila melanogaster*", Published in Chinese Bulletin of Life Sciences, vol. 27, Issue 5, May 2015, pp. 631-639.
Pierce, et al., "Ku DNA end-binding protein modulates homologous repair ofdouble-strand breaks in mammalian cells", In Journal of Genes and Development, Dec. 15, 2001, pp. 3237-3242.
Run-Chun, et al., "The Development of CRISPR/Cas9 System and Its Application in Crop Genome Editing", In Journal of Scientia Agriculture Sinica, vol. 49, Issue 7, Apr. 15, 2016, 1219-1229.
Si-Min, et al., "Classification and Selection of the Donor DNA in Genome Editing Technologies", In Chinese Journal of Biochemistry and Molecular Biology, vol. 33, Issue 1, Jan. 20, 2017, 10 Pages.
Stark, et al., "Genetic steps of mammalian homologous repair with distinct mutagenic consequences", Published in Molecular and Cell Biology, vol. 24, Issue 21, Nov. 2004, pp. 9305-9316.
Weichang, et al., "High-dimensional Space Digital Coding and Algorithm of DNA Sequence S4-10", In China-Japan Friendship Institute of Clinical Medicine, May 29, 2002, 3 Pages.
Zaboikin, et al., "Non-Homologous End Joining and Homology Directed DNA Repair Frequency of Double-Stranded Breaks Introduced by Genome Editing Reagents", In Journal of Plos One, Jan. 17, 2017, 36 Pages.
Zahir, et al., "Efficient Virus-Mediated Genome Editing in Plants Using the CRISPR/Cas9 System", In Journal of Molecular Plant, Aug. 3, 2015, pp. 1288-1291.
Zi-Zhi, et al., "Pathway choice for DNA double-strand break repair", In Chinese Bulletin of Life Sciences, vol. 26, Issue 11, Nov. 15, 2014, pp. 1172-1175.

* cited by examiner

MOLECULAR STATE MACHINES USING HDR TEMPLATE INSERTION

CROSS-REFERENCE TO RELATED APPLICATION

This application is a division of U.S. Patent Pub. No. 2018/0004537 filed on Jun. 16, 2007 entitled "Molecular State Machines." This application claims the benefit of U.S. Provisional Patent Application Ser. No. 62/357,828 filed on Jul. 1, 2016, entitled "Storage Through Iterative DNA Editing," U.S. Provisional Application Ser. No. 62/399,190 filed on Sep. 23, 2016, entitled "Storage Through Iterative DNA Editing," and U.S. Provisional Patent Application Ser. No. 62/487,671 filed on Apr. 20, 2017, entitled "Mechanisms for Molecular Event Logging" all of which are expressly incorporated herein by reference in their entirety. This application is related to U.S. Pat. No. 10,892,034 entitled "Timing of Logged Molecular Events" and U.S. Patent Pub. No. 2018/0002748 entitled "Barcodes for Identification of Gene Expression" both filed the same day as this application and the entirety of which are both expressly incorporated herein by reference.

BACKGROUND

A state machine provides a mathematical representation of behaviors that can be found in machines ranging from vending machines to computers. State machines respond to an input based on a current state of the machine. Thus, the behavior of a state machine depends on both the input received and the current state of the machine when that input is received. Synthetic biology, molecular computing, biological systems designed to log events, biological systems designed to store arbitrary information (e.g., digital data stored in DNA), and the like may all make use of state machines. A molecular state machine can open up new possibilities in these fields.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

This disclosure describes cells and cellular systems that can behave as state machines. The cells may record information, including a current state, by inserting homology directed repair (HDR) templates into double strand breaks (DSBs) in DNA or RNA through the process of HDR. Precise gene editing techniques such as CRISPR/Cas (Clustered regularly interspaced short palindromic repeats/CRISPR-associated protein) systems and TALEN (transcription activator-like effector nucleases) enable insertion of the HDR templates into a specific location in existing DNA or RNA.

Cells may also be set in a "state" by the presence of molecules that change the response of the cells to a given signal. The molecules may be applied externally to the cells or generated internally in response to stimuli (e.g., temperature, pH, light, chemicals, etc.). Once in a state, the cells may receive a signal indicating a molecular event, a binary digit to be recorded, or other task that is implemented by the cells in a way specific to the current state. Additionally, the cells may be changed from one state to a different state. The current state of cells may control which HDR template is integrated into DNA or RNA. Thus, the genetic record created in cells can be influenced by the state which enables the functions of a state machine.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
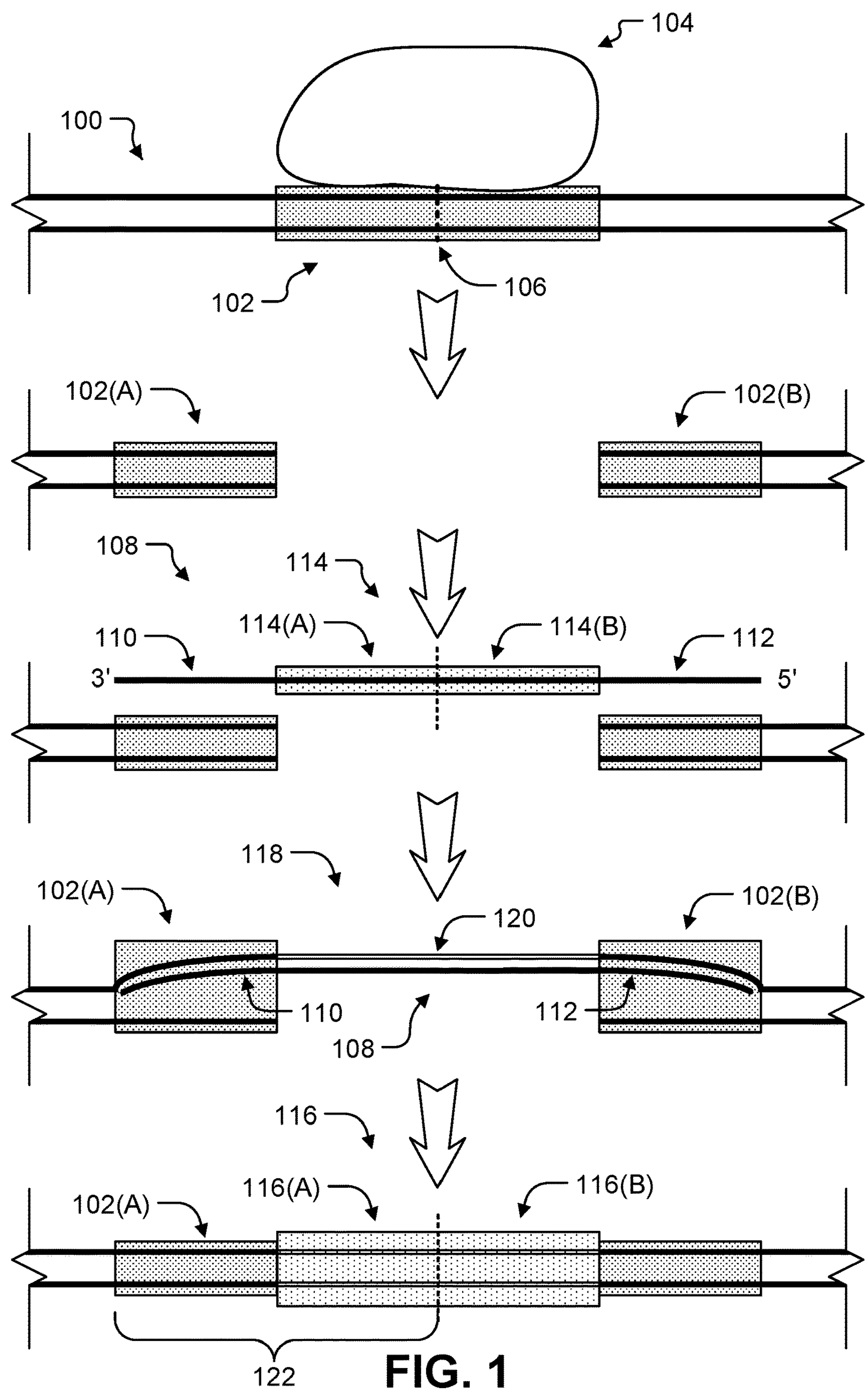
FIG. 1 shows a schematic representation of cutting DNA with an enzyme and inserting a polynucleotide sequence at the cut site by HDR.

This disclosure presents techniques for creating a molecular state machine in a cell. The molecular state machine changes the behavior of the cell according to a current state. Thus, responses of the cell to signals depend on both the signal and the context which is represented by the cell having a state. The cell may create a log of the molecular events sensed by the cell or record arbitrary information such as binary digits into genetic material of the cell creating a stable, heritable record. Specific homology directed repair templates are inserted into the genetic material of the cell to create the log or record arbitrary information. Sequencing the genetic material can retrieve the information for analysis or display on a computer. State machine functionality allows for more complex behavior such as logging events differently depending on the state of the cell or recording binary digits according to a context-dependent code in which the nucleotides used to represent a given digit (i.e., 1 or 0) depend not only on the digit but also on the previous digit.

The genetic material is a "polynucleotide" which is often DNA but may also be RNA or a hybrid combination of DNA and RNA. The polynucleotide may or may not include one or more artificial nucleotides (e.g., isoguanine, isocytosine, diaminopurine, etc.). References to "DNA" herein are understood to include all types of polynucleotides unless context specifically indicates otherwise. The molecular events sensed by the cell may be intra-cellular or extracellular events that results in generation of a signal that can be detected by a cellular system. Examples of molecular events include exposure to a chemical, a change in temperature, exposure to light (or dark), exposure to radiation, the presence of an antigen, a change in ionic concentration such as pH, etc. The molecular event may represent an external environmental condition or internal condition experienced by the cell.

The cellular system that detects the molecular event may include an extra-cellular receptor that responds to conditions outside the cell or an intra-cellular receptor that responds to conditions within the cell. The cellular system may communicate a signal detected by a receptor through a signaling pathway that ultimately results in modification of a polynucleotide. The signaling pathway may be an "engineered signaling pathway" that is a natural signaling pathway modified in part or an entirely synthetic pathway that is added to the cell. A signaling pathway may cause changes in a polynucleotide by controlling the expression of a gene product. Expression may be controlled by interaction between the signaling pathway and an inducible promoter. A promoter is a region of DNA that initiates transcription of a particular gene. In response to the signal, the signaling pathway may either turn on an inducible promoter, which increases transcription of the associated gene, or repress a promoter, which decreases transcription of the associated gene. The gene product from a gene controlled by the promoter is the component that is used to modify the polynucleotide. For example, the gene product may be an enzyme that cuts the polynucleotide or the gene product may be another polynucleotide that is used to modify a polynucleotide which already exists in the cell.

Modification of the polynucleotide in the cell may be performed through homology directed repair ("HDR"). HDR uses a template polynucleotide (usually DNA but RNA may also be used) to repair a double-stranded break ("DSB") in the polynucleotide. The repair removes the DSB and, based on the design of the template polynucleotide, referred to as an "HDR template" in this disclosure, may also add an additional polynucleotide sequence at the point of repair. Thus, a signal may cause a DSB to be created and then repaired through HDR in a way that adds a particular, additional polynucleotide sequence into the genetic material of the cell. Thereafter, presence of this polynucleotide sequence in the cell may cause the cell to be in a particular state, may be an indication that the cell has experienced a particular molecular event, may represent arbitrary information such as a binary digit. Design of engineered signaling pathways and HDR templates creates an arbitrary association between a particular signal and a particular polynucleotide sequence. Similarly, HDR may be used to add polynucleotide sequences that change the state of a cell by adding an insertion site for addition of another HDR template. Thus, the molecular mechanism for integrating a new sequence into a polynucleotide is the same, but the significance is different depending on whether the HDR template places the cell into a given state or the HDR template represents information that is stored in the polynucleotide.

By way of example only, a bacterial cell may be modified with a receptor that detects a particular chemical. The signal generated by that receptor may be passed through a signaling pathway to a promoter that increases the transcription of an HDR template that in turn adds a particular DNA sequence, e.g. ACTAGA, to the genomic DNA of the bacterial cell when repairing a DSB at a specific location. An enzyme creates the DSB at a predetermined position in the genomic DNA. The particular location of this DSB is specific based on the properties of the enzyme and is designed to be repaired by the corresponding HDR template. The chemical is detected by the receptor, which in turn leads to increased transcription of the HDR template. When many copies of the HDR template are present, one of those copies may be used to repair the DSB and add the sequence ACTAGA to the genomic DNA of the bacterial cell. Addition of the HDR template in response to detection of the chemical adds a new DNA sequence which itself may include a cut site for a different enzyme (e.g., there may be a cut site in the middle of the ACTAGA sequence). The presence of this cut site may be how a state is implemented for this cell. This other enzyme can create a DSB in the DNA added by the HDR template into which a second HDR template is inserted. The second HDR template can represent a binary digit or a log of a molecular event. The second HDR template may add, for example, the sequence GCT at the location of the cut site. This bacterial cell may be designed so that there are no cut sites for this other enzyme until after detection of the chemical and subsequent incorporation of the first HDR template. Thus, until the cell is in the correct state, the second HDR template cannot be inserted into the DNA. Later, analysis of the DNA of the bacterial cell by DNA sequencing can detect the sequence ACT-GCT-AGA which then serves as a record that the cell was exposed to this particular chemical and while the cell was in the state.

Homology Directed Repair

HDR is a mechanism in cells to repair DSBs. The most common form of HDR is homologous recombination. The HDR repair mechanism can be used by the cell when there is a homologous piece of DNA present to repair the DSB. HDR is considered a highly accurate mechanism for DSB repair due to the requirement of sequence homology between the damaged and intact donor strands of DNA. The process is nearly error-free if the DNA template used for repair is identical to the original DNA sequence at the DSB, or it can introduce very specific mutations into the damaged DNA if there are differences between the DNA template use for repair and the original DNA sequence. The HDR template may be contained in a plasmid and can contain 2-3 kb of homology surrounding the target sequence. The non-homologous portion of the HDR template at the target sequence can be altered to have the desired mutations or "knock-ins." The knock-in content may include selectable markers, fluorescent tags, a new cut site, etc. The plasmid containing an HDR template may be constructed by isolating the homologous region from genomic DNA by polymerase chain reaction (PCR) amplification and then cloned into a plasmid backbone. This disclosure discusses use of a homology repair template that adds a new DNA sequence at the point of the DSB as part of the repair process.

HDR includes homologous recombination (HR) and single-strand annealing (SSA) (Lieber. 2010 Annu. Rev. Biochem. 79:181-211). The most common form of HDR is HR which has the longest sequence homology requirements between the donor and acceptor DNA. Other forms of HDR include single-stranded annealing (SSA) and breakage-induced replication, and these require shorter sequence homology relative to HR. HDR at nicks (single-stranded breaks) can occur via a mechanism distinct from HDR at DSBs (Davis and Maizels. PNAS (0027-8424), 111 (10), p. E924-E932).

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

By "hybridizable" or "complementary" or "substantially complementary" it is meant that a polynucleotide (e.g. DNA or RNA) comprises a sequence of nucleotides that enables it to non-covalently bind, to another polynucleotide in a sequence-specific, antiparallel, manner (i.e., a polynucleotide specifically binds to a complementary polynucleotide) under the appropriate in vitro and/or in vivo conditions of temperature and solution ionic strength. As is known in the art.

Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein; and Sambrook, J. and Russell, W., *Molecular Cloning: A Laboratory Manual*, Third Edition, Cold Spring Harbor Laboratory Press, Cold Spring Harbor (2001). The conditions of temperature and ionic strength determine the "stringency" of the hybridization.

It is understood in the art that the sequence of polynucleotide need not be 100% complementary to that of its target polynucleotide to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target polynucleotide sequence to which they are targeted. For example, an antisense polynucleotide in which 18 of 20 nt of the antisense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. Percent complementarity between particular stretches of polynucleotide sequences within polynucleotides can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

FIG. 1 shows an illustrative schematic of operations to add a new DNA sequence into a double-stranded DNA (dsDNA) 100 through HDR. The new DNA sequence may become the record of a molecular event experienced by a cell containing the dsDNA 100. The dsDNA 100 includes a target site 102 that directs an enzyme 104 to create a DSB in the dsDNA 100 within the target site 102 at a specific cut site 106. The DSB may be created with blunt ends or with sticky ends depending on the specific enzyme and technique for making the DSB. The target site 102 is a sequence of DNA recognized by an enzyme that creates DSBs in dsDNA. By "enzyme reactive conditions" it is meant that any necessary conditions are available in an environment (i.e., such factors as temperature, pH, and lack of inhibiting substances) which will permit the enzyme to function. Enzyme reactive conditions can be either in vitro, such as in a test tube, or in vivo, such as within a cell.

The target site 102 may be intentionally introduced into the dsDNA 100 to enable the manipulations described below. Alternatively, a pre-existing portion of the dsDNA 100 may be selected as the target site 102. If a pre-existing portion of the dsDNA 100 is selected as the target site 102, then the sequence of other components of the system will be designed with reference to the sequence of the target site 102. In some implementations, the target site 102 is unique such that there is only one target site 102 in the entire dsDNA strand and/or only one target site 102 throughout all the DNA in the cell. The dsDNA 100 may be genomic DNA inside a living prokaryotic or eukaryotic cell, DNA introduced to a living cell such as a plasmid or vector, or DNA in a cell-free system. The dsDNA 100 may exist as either linear or circular DNA prior to introduction of the DSB.

The enzyme 104 that creates the DSB may be any protein, protein-RNA complex, or protein-DNA complex (including multimeric complexes) that has the property of creating a DSB in dsDNA at the cut site 106. Non-limiting examples of suitable enzymes include restriction enzymes, homing endonucleases, zinc-finger nucleases (ZFNs), transcription activator-like effector nucleases (TALENs), CRISPR/Cas, and NgAgo. These types of enzymes are all examples of site-specific nucleases that are capable of causing a DSB at a cut site 106 within a target site 102. Further details about site-specific nucleases are provided below.

After creating a DSB at the cut site 106, the target site 102 is split into two subsequences 102(A), 102(B) on either side of the DSB. Each of the two subsequences 102(A), 102(B) may, in an implementation, be between 5 and 20 nucleotides (nt) in length. Thus, the target site 102 may, in an implementation, be between 10 and 40 nt in length. In some implementations, the two subsequences 102(A), 102(B) may contain identical DNA sequences. The cut site 106 may be located in the middle of the target site 102 or it may be located elsewhere within the target site 102. The schematic shown in FIG. 1 illustrates a DSB with blunt ends, but as described above DSBs with sticky ends are also covered within the scope of this disclosure.

AN HDR template 108 is brought into proximity of the dsDNA 100 with the DSB. The HDR template 108 is single strand (ss) DNA or ssRNA. The HDR template repairs the DSB and inserts a polynucleotide sequence through the process of homology directed repair. HDR templates used to create specific mutations or insert new elements into a gene require a certain amount of homology surrounding the target site that will be modified. Thus, the HDR template 108 includes a 3'-end sequence 110 complementary to the first subsequence of the target site 102(A) and a 5'-end sequence 112 complementary to a second subsequence of the target site 102(B). Because they are complementary sequences, the length of the 3-end sequence 110 and the 5'-end sequence 112 are the same or about the same as the respective subsequences of the target site 102(A), 102(B). Thus, both 3-end sequence 110 and the 5'-end sequence 112 may be between 5 and 20 nt in length. The middle portion of the HDR template 108 contains a middle region 114 encoding a second target site 116. This middle region 114 may contain two subsequences 114(A), 114(B) on either side of the point where the second target site 116 will be cut by a second enzyme. The length of the two subsequences 114(A), 114(B) in the middle region 114 of the HDR template 108 may be different than the lengths of the two subsequences 102(A), 102(B) but may follow the same size range and be between five and 20 nt in length. Thus, the total length of the HDR template 108 may be between about 20 and 80 nt. Because the middle region 114 encodes a second target site 116, the HDR template 108 itself provides the basis for this process to be repeated iteratively. So long as a signal is detected by a cell and the components for creating a DSB and performing HDR are available, this process may continue until the signal ceases. Thus, a length of the inserted DNA may correlate with a duration of the signal.

The HDR template 108 then repairs the DSB through HDR. The efficiency of HDR may be low, and in some conditions, other repair mechanisms can predominate. The efficiency of HDR is determined in part by the concentration of donor DNA present at the time of repair, the length of the homology arms of the donor DNA, the cell cycle, and the activity of the endogenous repair systems. An overabundance of the HDR template 108 may be provided to increase efficiency of HDR. The overabundance of the HDR template 108 may be provided to a cell-free system by adding additional copies of the ssRNA or ssDNA manually or with the use of microfluidics. The HDR template 108 may also be provided, in overabundance if desired, by placing a gene encoding the HDR template 108 under control of a strong promoter and/or by having multiple copies of the gene encoding the HDR template 108 all undergoing transcription. In an implementation, this promoter may be regulated by a signaling pathway that responds to a signal. When the signal is detected, the promoter is turned on and more copies of the HDR template 108 are generated.

The 5'-ended DNA strand is resected at the DSB to create a 3' overhang. This will serve as both a substrate for proteins required for strand invasion and a primer for DNA repair synthesis. The HDR template 108 can then displace one strand of the homologous DNA duplex and pair with the other; this causes formation of hybrid DNA referred to as the displacement loop ("D loop") 118. The recombination intermediates can then be resolved to complete the DNA repair process. As mentioned above, an overabundance of the HDR template 108 may be provided. One of ordinary skill in the art will understand how to perform HDR with dsDNA 100 having a DSB and an HDR template 108. Possible protocols for performing HDR are provided in Jie Liu et al., In Vitro Assays for DNA Pairing in Recombination Associated DNA Synthesis, 745 Methods Mol. Bio. 363 (2011); Gratz, S. et al., Highly specific and efficient CRISPR/Cas9-catalyzed homology-directed repair in Drosophila, 196 Genetics 967 (2014); Richardson, C. C. et al., Enhancing homology-directed genome editing by catalytically active and inactive CRISPR-Cas9 using asymmetric donor DNA, 34 Nature Biotechnology 399 (2016); and Lin, S. et al., Enhanced homology-directed human genome engineering by controlled timing of CRISPR/Cas9 delivery, eLIFE (2014).

After the HDR template 108 invades the dsDNA, the D loop 118 is formed by hybridization of the 3'-end sequence 110 to the first subsequence 102(A) of the target site 102 and hybridization of the 5'-end sequence 112 to the second subsequence 102(B) of the target site 102. DNA polymerase synthesizes new ssDNA 120 complementary to the middle region 114 of one strand of the dsDNA 100. DNA ligase joins the sugar-phosphate backbone of the newly synthesized ssDNA 120 with the remainder of that strand of the dsDNA 100. This forms one strand of the second target site 116.

Hybridization requires that the two polynucleotides contain complementary sequences, although mismatches between bases are possible. The conditions appropriate for hybridization between two polynucleotides depend on the length of the polynucleotides and the degree of complementation which are variables well known in the art. The greater the degree of complementation between two nucleotide sequences, the greater the value of the melting temperature ($T_m$) for hybrids of polynucleotides having those sequences. For hybridizations between polynucleotides with short stretches of complementarity (e.g. complementarity over 35 nt or less, 30 nt or less, 25 nt or less, 22 nt or less, 20 nt or less, or 18 nt or less) the position of mismatches becomes important. This is understood by one of ordinary skill in the art and described in Sambrook, J. and Russell, W., *Molecular Cloning: A Laboratory Manual*, Third Edition, Cold Spring Harbor Laboratory Press, Cold Spring Harbor (2001) at sec. 11.7-11.8. Typically, the length for a hybridizable polynucleotide is at least about 10 nt. Illustrative minimum lengths for a hybridizable polynucleotide are: at least about 15 nt; at least about 20 nt; at least about 22 nt; at least about 25 nt; and at least about 30 nt). Furthermore, the skilled artisan will recognize that the temperature, pH, and wash solution salt concentration may be adjusted as necessary according to factors such as length of the region of complementation and the degree of complementation.

Following repair of the first strand of the dsDNA 100, the second strand of the dsDNA 100 is repaired by DNA polymerase and DNA ligase using the sequence of the new ssDNA 120 in the repaired, first strand as a template. This completes the repair of the dsDNA 100 resulting in dsDNA that includes the second target site 116 inserted within the first target site 102.

DNA polymerases are enzymes that synthesize DNA molecules from individual deoxyribonucleotides. During this process, DNA polymerase "reads" an existing DNA strand to create a new, complementary strand. DNA ligase is a specific type of enzyme, a ligase, that facilitates the joining of DNA strands together by catalyzing the formation of a phosphodiester bond. It plays a role in repairing single-strand breaks. The mechanism of DNA ligase is to form two covalent phosphodiester bonds between 3' hydroxyl ends of one nucleotide, ("acceptor") with the 5' phosphate end of another ("donor"). The DNA ligase from bacteriophage T4 is the ligase most-commonly used in laboratory research. It can ligate cohesive or "sticky" ends of DNA, oligonucleotides, as well as RNA and RNA-DNA hybrids, but not single-stranded polynucleotides. It can also ligate blunt-ended DNA.

Note that the HDR template 108 includes two types of regions: end regions and a middle region. The end regions are homologous to one of the strands of the dsDNA 100 on either side of the DSB. Here, the homologous regions are shown by the 3-end sequence 110 and the 5'-end sequence 112. The homology need not be 100% but only to the extent that the 3'-end sequence 110 and the 5'-end sequence 112 hybridize to one strand of the dsDNA 100. The middle region is the middle region 114 of the HDR template 108 that encodes the sequence of the second target site 116. Independently varying both the end regions and the middle region allows for creation of multiple different HDR templates 108 from a relatively limited set of end regions and middle regions. Thus, the middle region of an inserted HDR template 108 need not have the same target site 102 or cut site 106 as the dsDNA 100 it is being inserted into.

Following HDR, the dsDNA 100 includes the first subsequence 102(A) of the first target site 102 followed by the first subsequence 116(A) of the second target site 116. The DNA sequence 122 represented by this order of the two subsequences 102(A), 116(A) of the two target sites may represent a particular signal combination (e.g., temperature above 30° C. followed by pH under 5). As mentioned above, a length of the subsequence 102(A) is from five to 20 nt and the length of the subsequence 114(A) is also from five to 20 nt. Thus, in an implementation, the total length of the DNA sequence 122 is from 10 to 40 nt.

HDR, however, is not the only way to repair a DSB. Non-Homologous End-Joining (NHEJ) is a pathway that repairs double-strand breaks in DNA and may be favored over HDR in many conditions. NHEJ is referred to as "non-homologous" because the break ends are directly ligated without the need for a homologous template. NHEJ is active throughout the cell cycle and has a higher capacity for repair, as there is no requirement for a repair template (sister chromatid or homologue) or extensive DNA synthesis. NHEJ also finishes repair of most types of breaks in tens of minutes—an order of magnitude faster than HDR. Thus, in many cells there is competition between HDR and NHEJ. If the ratio of HDR to NHEJ is high enough, HDR will continue. However, in the presence of NHEJ some of the DSBs formed by the enzyme 104 will rejoin without an insert.

NHEJ is consequently the principle means by which DSBs are repaired in natural cells. NHEJ-mediated repair is prone to generating indel errors. Indel errors generated in the course of repair by NHEJ are typically small (1-10 nt) but extremely heterogeneous. There is consequently about a two-thirds chance of causing a frameshift mutation. Thus, it may be desirable to minimize NHEJ and increase the probability that a DSB will be repaired by HDR. The likelihood of HDR being used may be improved by inhibiting components of the NHEJ process. Addition of small molecules such as NU7441 and KU-0060648 is one technique for inhibiting NHEJ through inhibition of DNA-dependent protein kinase, catalytic subunit ("DNA-PKcs"). Techniques for enhancing HDR efficiency in this way are described in Maruyama, et al., *Increasing the efficiency of precise genome editing with CRISPR-Cas9 by inhibition of nonhomologous end joining.* 33(5) Nature Biotechnology, 538 (2015) and Robert, et. al., *Pharmacological inhibition of DNA-PK stimulates Cas9-mediated genome editing.* 7 Genome Medicine 93 (2015). In an implementation, HDR efficiency may be improved by suppressing the molecules KU70, KU80, and/or DNA ligase IV, which are involved in the NHEJ pathway. In addition to the suppression, the Cas9 system, E1B55K, and/or E4orf6 may be expressed to further increase HDR efficiency and reduce NHEJ activity. Techniques for enhancing HDR efficiency in this way are described in Chu et al., *Increasing the efficiency of homology-directed repair for CRISPR-Cas9-induced precise gene editing in mammalian cells.* 33(5) Nature Biotechnology, 543 (2015). Further, use of a single-stranded DNA oligo donor (ssODN) has been shown to improve the rate of HDR and knockin efficiency by up to 60% in Richardson et al., *Enhancing homology-directed genome editing by catalytically active and inactive CRISPR-Cas9 using asymmetric donor DNA,* 34(3) Nature Biotechnology 339 (2016).

Figure 2:
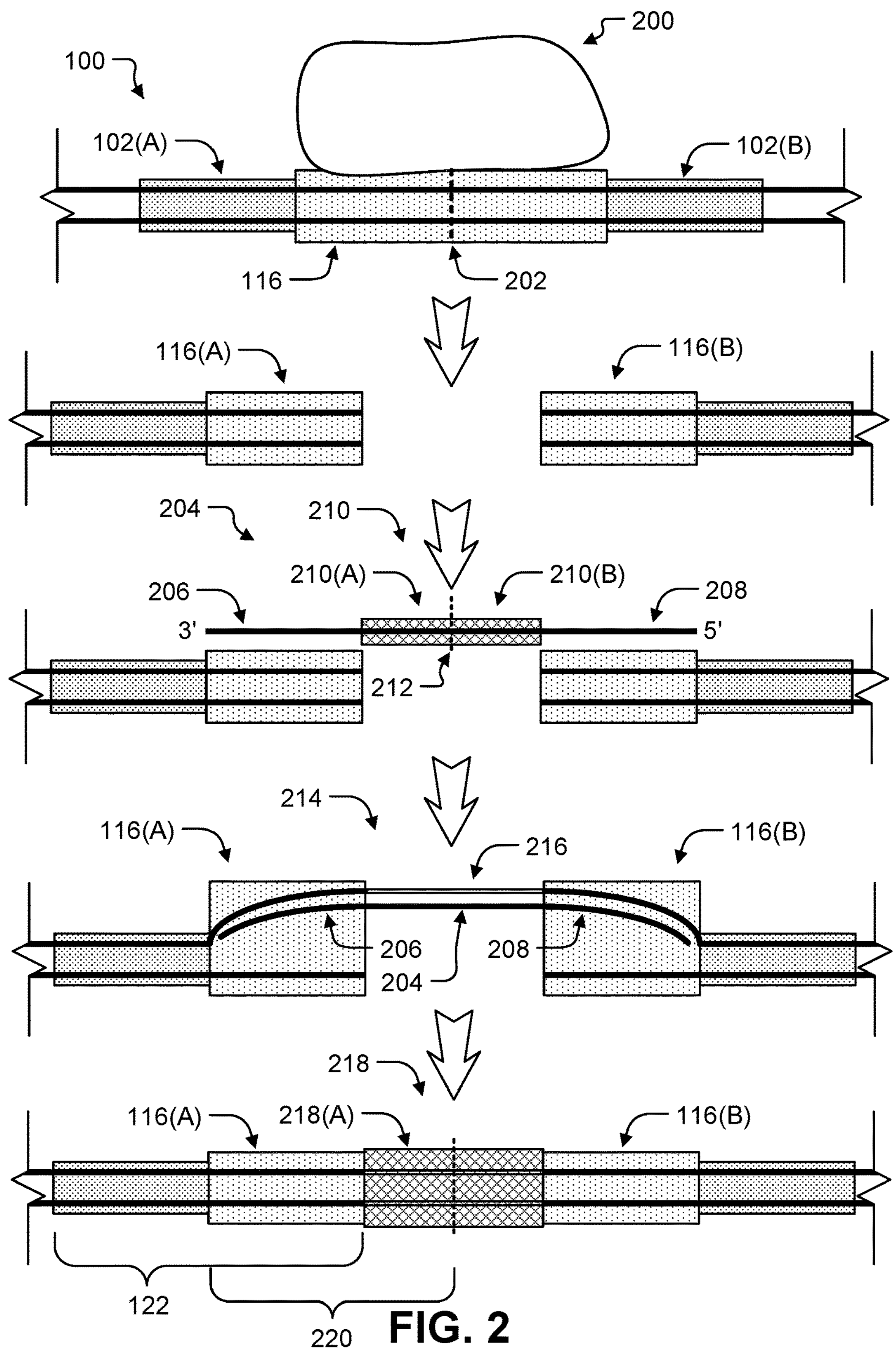
FIG. 2 shows a schematic representation of cutting the DNA of FIG. 1 and inserting an additional polynucleotide sequence by additional HDR.

FIG. 2 shows schematic illustrations of further manipulations performed on the dsDNA 100 molecule of FIG. 1. A second enzyme 200 creates a second DSB at a second cut site 202 in the second target site 116. The second target site 116 has a different sequence than the first target site 102, and thus, the second enzyme 200 recognizes a different DNA sequence than the first enzyme 104. Creating a DSB in the second target site 116 at the cut site 202 creates the first subsequence 116(A) of the second target site 116 on one side of the cut site 202 and a second subsequence 116(B) of the second target site 116 on the other side of the cut site 202. In some implementations, the first subsequence 116(A) and the second subsequence 116(B) may have the same sequence. Thus, the first subsequence 116(A) and a second subsequence 116(B) may have the same nucleotide length. Also, if the first subsequence 116(A) and the second subsequence 116(B) are the same sequence, the second target site 116 may be thought of as having a single subsequence repeated once with a cut site 202 in the middle.

A second HDR template 204 contacts the dsDNA 100 to provide a template for HDR of the DSB. The second HDR template 204 includes a 3'-end region 206 that is homologous to one strand of the dsDNA 100 within the first subsequence 116(A) of the second target site 116. The second HDR template 204 also include a 5'-end region 208 that is homologous to one strand of the dsDNA 100 within the second subsequence 116(B) of the second target site 116. The second HDR template 204 also includes a portion in the middle region 210 that encodes a third target site for a third enzyme. The middle region 210 includes a first subsequence 210(A) on one side of a third cut site 212 and a second subsequence 210(B) on other side of the third cut site 212.

Annealing of the second HDR template 204 to one strand of the dsDNA 100 creates a D loop 214 by hybridization of the 3'-end region 206 to the subsequence 116(A) and hybridization of the 5'-end region 208 to the subsequence 116(B). DNA polymerase and DNA ligase repair the strand of the dsDNA 100 to which the second HDR template 204 is hybridized by creating new DNA 216. The second strand of the dsDNA 100 is then repaired using the first strand as a template.

The dsDNA 100 now includes the third target site 218 inserted into the middle of the second target site 116 (which is itself inserted in the middle of the first target site 102). The order of the subsequence 116(A) followed by the subsequence 218(A) may create a record of a second combination of detected signals or a particular binary digit. Thus, the growing string of inserted DNA sequences can provide an ordered log of molecular events experienced by a cell or store arbitrary information such as binary digits. This process can repeat to record any number of molecular events or any length of digital data.

Addition of HDR templates into existing DNA using the mechanisms described above may be regulated by signaling pathways as described in detail below. The encoding scheme described herein allows for insertion of DNA sequences representing an unbounded length. An HDR template that does not include a cut site may be added ending the process of HDR because there are no further cut sites. The dsDNA in a cell may have multiple different target sites at different locations that include different cut sites and are homologous to different HDR templates. This provides for orthogonal recording of signals without any linkage between the signals. This type of orthogonal relationship allows for a cell to implement multiple state machines that function independently of each other. A cell may be modified to have any number of orthogonal target sites.

The three target sites may be represented as $X_1X_2$, $Y_1Y_2$, and $Z_1Z_2$. The first portion of the target site (e.g., $X_1$, $Y_1$, or $Z_1$) corresponds to subsequence 102(A) or subsequence 116(A) shown in FIG. 1. The remaining portion of the target site (e.g., $X_2$, $Y_2$, or $Z_2$) corresponds to subsequence 102(B) or subsequence 116(B) shown in FIG. 1. Thus, each X, Y, and Z represents a DNA sequence of about 5 to 20 nt such as, for example only, ACTGAA, GCCTCAT, TGACG, etc. In some implementations $X_1=X_2$, etc., but in other implementations the first portion of a target site may be different in sequence and/or length from the remaining portion of the target site.

The HDR templates all have end regions that are homologous to one of the target sites. Thus, the HDR templates will have sequences of the structure: $X_1aX_2$, $Y_1bY_2$, and $Z_1cZ_2$ where "a," "b," and "c" represent DNA sequences of the middle regions. Recall that the middle region of the HDR templates may itself encode a target site. Thus, for example, "a" may represent $X_1X_2$, "b" may represent $Z_1Z_2$, and "c" may represent a different target site $W_1W_2$. If the middle region does encode a target site, integration of an HDR template into dsDNA may be followed by further integration of the same or a different HDR template. Insertion of an HDR template into dsDNA that has been itself created by integration of an HDR template is referred to in this disclosure as "iterative integration."

In one configuration, the continued detection of multiple signals may be recorded by appropriately designed HDR templates and insertion sites. An HDR template with a sequence XaYYaX is expressed when a first signal "a" is detected. Similarly, an HDR template YbXXbY is expressed when a second signal "b" is detected. Initially, the cell may include either a target site XX or YY depending on the current state of the cell. If the cell only includes the target site XX, presence of signal "b" will not be recorded until the state of the cell changes so that a target site YY is made available in the DNA of the cell.

In one configuration, multiple signals may be associated with HDR templates that have the same target sites. For example, a first signal "a" and a second signal "b" may be associated respectively with the HDR templates XaXXaX and XbXXbX. Either HDR template may be integrated into the target site XX. Once integrated, both HDR templates also include the target site XX allowing for iterative addition of either or both. The state of the cell may control which HDR template is available. For example, in a first state the HDR template XaXXaX may be available. In a second state, the HDR template XbXXbX may be available.

Each class of HDR template includes two (but may include any number) HDR templates with partially different sequences that correspond to different signals. Thus, a signal "$a_1$" may cause increased expression of the HDR template $Xa_1YYa_1X$ and a signal "$a_2$" may cause increased expression of the HDR template $Xa_2YYa_2X$. Similarly, a signal "$b_1$" may cause increased expression of the HDR template $Yb_1XXb_1Y$ and a signal "$b_2$" may cause increased expression of the HDR template $Yb_2XXb_2Y$. If the cell begins with DNA that includes the insertion site XX, then first one of the "a" HDR templates will be integrated based on the relative concentrations of the $Xa_1YYa_1X$ and of the $Xa_2YYa_2X$ HDR templates.

In one example implementation, using Cas9 as the nuclease with a PAM sequence of NNNNGATTT as the enzyme, three target sites may be:

$X_1$ = TAGCCGTATCGAGCATCGATG | CGCNNNNGATT = $X_2$ $Y_1$ = GATCGATGGACTCTGCATCTA | TCGNNNNGATT = $Y_2$ $Z_1$ = CGGGACGATCGATCGGGCTAG | ACTNNNNGATT = $Z_2$

Where the PAM sequence is indicated by bold, $X_1$ is (SEQ ID NO: 1), $X_2$ is (SEQ ID NO: 2), $Y_1$ is (SEQ ID NO: 3), $Y_2$ is (SEQ ID NO: 4), $Z_1$ is (SEQ ID NO: 5), and $Z_2$ is (SEQ ID NO: 6). Note that each of $X_1$, $Y_1$, and $Z_1$ are 21 nt long.

Each of the target sites is recognized by a corresponding guide ssDNA that cuts the dsDNA at the location indicated by the "^" below. They should have a trans-activating crRNA (tracrRNA) that is a small trans-encoded RNA for attaching to Cas9 appended to the end. The crRNAs are incorporated into effector complexes, where the crRNA guides the complex to the target site and the Cas proteins create a DSB in the polynucleotide. The respective ssDNA sequences are:

(SEQ ID NO: 1)
$gX_1$ = TAGCCGTATCGAGCATCGATG ^ CGC (SEQ ID NO: 3)
$gY_1$ = GATCGATGGACTCTGCATCTA ^ TCG (SEQ ID NO: 5)
$gZ_1$ = CGGGACGATCGATCGGGCTAG ^ ACT

Then a homology directed repair sequence of $X_1Y_1Y_2X_2$ is: TAGCCGTATCGAGCATCGATG|GATCGATGGACTCTGCATCTA|TCGNNNNGATT|CGCNNNNGATT (SEQ ID NO: 7) and a homology directed repair sequence of $Y_1X_1X_2Y_2$ is: GATCGATGGACTCTGCATCTA|TAGCCGTATCGAGCATCGATG|CGCNNNNGATT|TCGNNNNGATT (SEQ ID NO: 8). Other homology directed repair sequences can be designed according to the same pattern.

An initial cut of the target site $X_1X_2$ will create a DSB that appears as (only one strand of the dsDNA is shown):

. . . TAGCCGTATCGAGCATCGATG CGCNNNNGATT . . .

After HDR with $X_1Y_1Y_2X_2$, one strand of the dsDNA will have the following sequence that now includes the target site $Y_1Y_2$ indicated by italics:

(SEQ ID NO: 7)
TAGCCGTATCGAGCATCGATG | *GATCGATGGACTCTGCATCTA* ||
*TCGNNNNGATT* | CGCNNNNGATT.

The dsDNA is now able to be cut by a Cas9 that has $Y_1$ creating a DSB at the location represented by "||". HDR may be performed with $Y_1X_1X_2Y_2$, for example, further adding to the dsDNA and completing another iteration of encoding. This may be continued with various sequences of cuts and HDR templates to record any series of molecular events.

Figure 3:
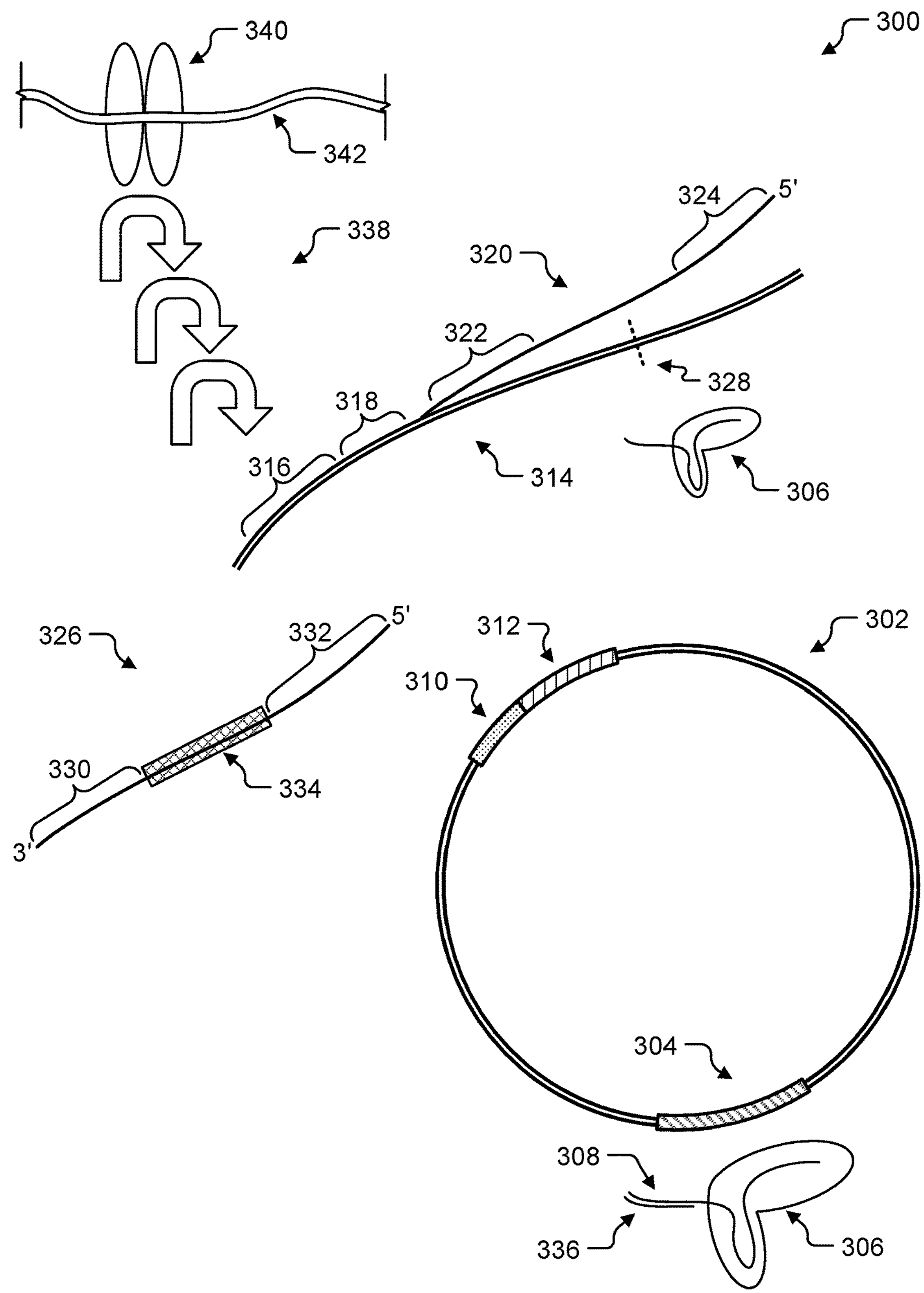
FIG. 3 shows illustrative components of a cell for inserting a polynucleotide sequence into existing DNA.

FIG. 3 shows components of an illustrative cell 300 that is capable of integrating new DNA into existing dsDNA as described in FIGS. 1 and 2. The cell 300 may be an *E. coli* cell, a *S. cerevisiae* cell, or a cell from another single-celled organism. It may also be a cell from a multi-cellular organism grown in culture.

The cell 300 may contain a dsDNA molecule 302 that has a first target site 304. The cell 300 may also contain a first enzyme 306 that is configured to create a DSB at a cut site within the first target site 304. For example, the first enzyme 306 may be a CRISPR/Cas system comprising a guide RNA (gRNA) 308 that includes a spacer region (also called a proto-spacer element or targeting sequence) of about 20 nt that is complementary to one strand of the dsDNA molecule 302 at the first target site 304. The *S. pyogenes* Cas9 system from the CRISPR-Cas family is one example of an effective genome engineering enzyme that catalyzes DSBs and generates mutations at DNA loci targeted by a gRNA. The native gRNA is comprised of a 20 nt Specificity Determining Sequence (SDS), which specifies the DNA sequence to be targeted, and is immediately followed by a 80 nt scaffold sequence, which associates the gRNA with Cas9. In addition to sequence homology with the SDS, targeted DNA sequences possess a Protospacer Adjacent Motif (PAM) (5'-NGG-3') immediately adjacent to their 3'-end in order to be bound by the Cas9-sgRNA complex and cleaved. When a DSB is introduced in the target DNA locus in the genome, the break is repaired by either homologous recombination (when a repair template is provided) or error-prone non-homologous end joining (NHEJ) resulting in mutagenesis of the targeted locus. Even though the normal DNA locus encoding the gRNA sequence is perfectly homologous to the gRNA, it is not targeted by the standard Cas9-gRNA complex because it does not contain a PAM.

In a wild-type CRISPR/Cas system, gRNA is encoded genomically or episomally (e.g., on a plasmid). Following transcription, the gRNA forms a complex with Cas9 endonuclease. This complex is then "guided" by the specificity determining sequence (SDS) of the gRNA to a DNA target sequence, typically located in the genome of a cell. For Cas9 to successfully bind to the DNA target sequence, a region of the target sequence must be complementary to the SDS of the gRNA sequence and must be immediately followed by the correct protospacer adjacent motif (PAM) sequence (e.g. "NGG"). Thus, in a wild-type CRISPR/Cas9 system, the PAM sequence is present in the DNA target sequence but not in the gRNA sequence (or in the sequence encoding the gRNA).

The PAM sequence is typically a sequence of nucleotides located adjacent to (e.g., within 10, 9, 8, 7, 6, 5, 4, 3, 3, or 1 nt) an SDS sequence). A PAM sequence is "immediately adjacent to" an SDS sequence if the PAM sequence is contiguous with the SDS sequence (that is, if there are no nucleotides located between the PAM sequence and the SDS sequence). In some implementations, a PAM sequence is a wild-type PAM sequence. Examples of PAM sequences include, without limitation, NGG, NGR, NNGRR(T/N), NNNNGATT, NNAGAAW, NGGAG, and NAAAAC, AWG, CC. In some implementations, a PAM sequence is obtained from *Streptococcus pyogenes* (e.g., NGG or NGR). In some implementations, a PAM sequence is obtained from *Staphylococcus aureus* (e.g., NNGRR(T/N)). In some implementations, a PAM sequence is obtained from *Neisseria meningitidis* (e.g., NNNNGATT). In some implementations, a PAM sequence is obtained from *Streptococcus thermophilus* (e.g., NNAGAAW or NGGAG). In some implementations, a PAM sequence is obtained from *Treponema denticola* NGGAG (e.g., NAAAAC). In some implementations, a PAM sequence is obtained from *E. coli* (e.g., AWG). In some implementations, a PAM sequence is obtained from *Pseudomonas auruginosa* (e.g., CC). Other PAM sequences are contemplated. A PAM sequence is typically located downstream (i.e., 3') from the SDS, although in some embodiments a PAM sequence may be located upstream (i.e., 5') from the SDS.

The dsDNA molecule 302 may also include a promoter 310 and a gene 312 encoding a homology-directed repair template such as HDR template 326 shown in this figure, an enzyme such as the first enzyme 306, a gRNA such as the gRNA 308, etc. The dsDNA molecule 302 may be a vector or plasmid.

A "vector" is a polynucleotide molecule, such as a DNA molecule derived, for example, from a plasmid, bacteriophage, yeast or virus, into which a polynucleotide can be inserted or cloned. One type of vector is a "plasmid," which refers to a circular dsDNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, lentiviruses, replicative defective lentiviruses, adenoviruses, replication defective adenoviruses, and adeno-associated viruses). Viral vectors also include polynucleotides carried by a virus for transfection into a host cell. Moreover, certain vectors are capable of directing the expression of genes to which they are operatively-linked. Such vectors are referred to herein as "expression vectors." Common expression vectors of utility in recombinant DNA techniques are often in the form of plasmids. Plasmids, methods for inserting nucleic acid sequences into a plasmid, and methods for delivering recombinant plasmids to cells of interest are known in the art.

A vector may contain one or more unique restriction sites and can be capable of autonomous replication in a defined host cell including a target cell or tissue or a progenitor cell or tissue thereof (e.g. bacterial vectors having a bacterial origin of replication and episomal mammalian vectors), or be integrable with the genome of the defined host such that the cloned sequence is reproducible (e.g., non-episomal mammalian vectors). Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. Such a vector may comprise specific sequences that allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants.

Vectors can be designed for expression of transcripts (e.g. nucleic acid transcripts, proteins, or enzymes) in prokaryotic or eukaryotic cells. For example, transcripts can be expressed in bacterial cells such as *E. coli*, insect cells (using baculovirus expression vectors), yeast cells, or mammalian cells. Suitable host cells are discussed further in Goeddel, *Gene Expression Technology: Methods In Enzymology,* 185, Academic Press. San Diego, Calif. (1990). Alternatively, a recombinant expression vector can be transcribed and translated in vitro, for example using T7 promoter regulatory sequences and T7 polymerase.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). Expression of proteins in prokaryotes is most often carried out in *E. coli* with vectors containing constitutive or inducible promoters directing the expression of proteins. Examples of suitable inducible *E. coli* expression vectors include pTrc (Amrann et al., (1988) Gene 69:301-315) and pET 11d (Studier et al., *Gene Expression Technology: Methods In Enzymology,* 185 Academic Press, San Diego, Calif. 60 (1990)).

In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). For other suitable expression systems for both prokaryotic and eukaryotic cells see, e.g., Chapters 16 and 17 of Sambrook, et al., *Molecular Cloning: A Laboratory Manual.* 2nd ed., Cold Spring Harbor Laboratory, Cold Spring Harbor Laboratory Press, Cold Spring Harbor, N.Y., 1989.

Cells, such as cells in culture, may be transfected or transformed with the dsDNA molecule 302. Transfection is the process of deliberately introducing naked or purified polynucleotides into eukaryotic animal cells. Transformation refers to DNA transfer in bacteria and non-animal eukaryotic cells, including plant cells. Transfection may be performed using viruses or mechanical methods. Viral transfection introduces foreign DNA into a cell by a virus or viral vector. Transfection with a virus may introduce the DNA into the genome of the host cell. Mechanical transfection typically involves opening transient pores or "holes" in the cell membrane to allow the uptake of material. Transfection can be carried out using calcium phosphate (i.e. tricalcium phosphate), by electroporation, microinjection, gene gun, impalefection, hydrostatic pressure, continuous infusion, sonication, lipofection, nanoparticles containing the dsDNA molecule 302 (e.g., mesoporous silica nanoparticles or gold nanoparticles) or by mixing a cationic lipid with the material to produce liposomes which fuse with the cell membrane and deposit their cargo inside. Nanoparticles used to introduce foreign DNA may be ionically charged or have targeting ligands to deliver to specific cells or sites.

One viral transfection technique for transferring genetic material to hard-to-transfect cells is recombinant adeno-associated virus (AAV) delivery. This is a type of viral transduction that does not integrate into the host genome. AAV-based systems have been used successfully to introduce the gene for *S. pyogenes* Cas9 (SpCas9) together with its optimal promoter and polyadenylation signal using the AAVpro CRISPR/Cas9 Helper Free System (AAV2) available from Takara Bio USA, Inc.

Conjugation may also be used to introduce the dsDNA molecule 302 into a cell. Although conjugation in nature occurs more frequently in bacteria, transfer of genetic material from bacterial to mammalian cells is also possible. See Waters V. L., *Conjugation between bacterial and mammalian cells.* 29(4) Nature Genetics 375 (2001).

The cell 300 may also include an operon 314 including of a promoter 316 and an operator 318. The operon 314 may encode a gene that is transcribed into a ssRNA sequence 320 comprising a 3'-end sequence 322 and a 5'-end sequence 324. An HDR template 326 may be generated from the ssRNA sequence 320. In one implementation, the HDR template 326 is the ssRNA sequence 320 itself. The 3'-end sequence 322 and the 5'-end sequence 324 may be complementary to one strand of the dsDNA molecule 302 over at least part of the target site 304. Homology between the 3'-end sequence 322 and the 5'-end sequence 324 allows the ssRNA sequence 320 to hybridize with portions of the dsDNA on either side of a DSB created at a cut site in the target site 304.

In implementations in which the operon 314 directly encodes the HDR template 326, the operon 314 will encode a cut site 328 that may be cut by an enzyme such as the first enzyme 306. Unless protected from the enzyme, the cut site 328 in the operon 314 may be unintentionally cut when the enzyme contacts the DNA of the operon 314.

One technique for protecting the cut site 328 from an enzyme is physical separation. In a cell-free system, such as one that uses microfluidics, the operon 314 may be maintained in one chamber and the ssRNA sequence 320 may be moved from the chamber containing the operon 314 into a different chamber where the enzyme is present.

Physical separation may also be used in cellular implementations. The operon 314 and the enzyme may be contained in different cellular chambers. In one implementation, the operon 314 may be in the nucleus and the enzyme may be outside the nucleus in the cytoplasm or in another cellular chamber. The operon 314 may remain in the nucleus if it is part of the cell's genome. A nuclear export signal (NES) may be used to keep the enzyme, or other component of the system, out of the nucleus. A NES is a short amino acid sequence of four hydrophobic residues in a protein that targets it for export from the cell nucleus to the cytoplasm through the nuclear pore complex using nuclear transport. Similarly, a nuclear localization signal (NLS) may be used to keep the enzyme, or other protein, in the nucleus. A NLS is an amino acid sequence that tags a protein for import into the cell nucleus by nuclear transport. Typically, a NLS consists of one or more short sequences of positively charged lysines or arginines exposed on the protein surface. Different nuclear localized proteins may share the same NLS. An NLS has the opposite function of a NES. Persons of ordinary skill in the art will be able to modify or engineer a protein such as a nuclease or other enzyme to include a NES or a NLS.

The physical location of RNA in a cell may also be controlled. The ssRNA sequence 320 may be exported from its site of transcription in the nucleus to the cytoplasm or other destination outside the nucleus where the first enzyme 306 is present. RNA export is described in Sean Carmody and Susan Wente, *mRNA Nuclear Export at a Glance,* 122

J. of Cell Science 1933 (2009) and Alwin Köhler and Ed Hurt, *Exporting RNA from the Nucleus to the Cytoplasm,* 8 Nature Reviews Molecular Cell Biology 761 (2007).

Splicing may be used in place of or in addition to physical separation to protect the operon 314 from being cut by the first enzyme 306. In one implementation, the operon 314 may include a sequence with a portion that is later removed by splicing. This additional portion changes the sequence of nucleotides in the operon 314 so that there is no cut site 328 present. The ssRNA sequence 320 will becomes an HDR template 326 through splicing, which also introduces the cut site 328.

Alternative splicing, or differential splicing, is a regulated process during gene expression that results in a single gene coding for multiple proteins. In this process, particular exons of a gene may be included within or excluded from the final, processed messenger RNA (mRNA) produced from that gene. Consequently, the proteins translated from alternatively spliced mRNAs will contain differences in their amino acid sequence and, often, in their biological functions. The production of alternatively spliced mRNAs is regulated by a system of trans-acting proteins that bind to cis-acting sites on the primary transcript itself. Such proteins include splicing activators that promote the usage of a particular splice site, and splicing repressors that reduce the usage of a particular site. There are multiple types of alternative splicing including exon skipping, mutually exclusive exons, alternative donor sites, alternative acceptor sites, and intron retention. Exon skipping is one way to cause splicing in the ssRNA sequence 320; in this case, an exon may be spliced out of the primary transcript. Persons having ordinary skill in the art will understand how to design the operon 314 so that it includes a splice site at a specified location. Alternative splicing may be implemented as a technique to prevent creation of a DSB in the operon 314 even if the operon 314 and enzyme 306 are not physically separated.

Self-excising elements may function similarly to splicing. The operon 314 may be designed to include a region that, when transcribed into RNA, includes one or more self-excising elements. Inclusion of the self-excising elements, for example in a way that disrupts the cut site 328, prevents the operon 314 from being recognized by the enzyme 306 and the excision converts the ssRNA sequence 320 into the HDR template 326. One type of self-excising elements are ribozymes, which are RNA enzymes that function as reaction catalysts. Ribozymes are RNA sequences that catalyze a (trans-esterification) reaction to remove the ribozyme sequence itself from the rest of the RNA sequence. Essentially these are considered introns, which are intragenic regions spliced from mRNA to produce mature RNA with a continuous exon (coding region) sequence. Self-excising introns/ribozymes consist of group I and group II introns. Many group I introns in bacteria are known to self-splice and maintain a conserved secondary structure comprised of a paired element which uses a guanosine (GMP, GDP, or GTP) cofactor. An example of a group I intron is the *Staphylococcus* phage twort.ORF143. Group I and group II introns are considered self-splicing because they do not require proteins to initialize the reaction. Self-excising sequences are known and one of ordinary skill in the art will understand how to include a self-excising sequence in the operon 314. Aspects of self-excising ribozymes are shown in In Vivo Protein Fusion Assembly Using *Self Excising Ribozyme* available at 2011.igem.org/Team:Waterloo (last visited Mar. 3, 2017).

A series of homologous bridges may also be used to generate a recombinant sequence that is the gene template for the ssRNA sequence 320. The homologous bridges may be present in the DNA at various, separate locations so that the operon 314 does not include a cut site 328. This technique is also known as multi-fragment cloning or extension cloning. The final HDR template 326 is made up of transcripts of the multiple overlapping segments. One suitable technique for combining the multiple-overlapping fragments into the HDR template 326 is Sequence and Ligation-Independent Cloning (SLIC). This technique is described in Mamie Li and Stephen Elledge, *Harnessing Homologous Recombination in vitro to Generate Recombinant DNA Via SLIC,* 4 Nature Methods 250 (2007). Another suitable technique for joining multiple-overlapping fragments is provided by Jiayuan Quan and Jingdong Tian, *Circular Polymerase Extension of Cloning of Complex Gene Libraries and Pathways,* 4(7) PLoS ONE e6441 (2009).

Methylation may be used to protect HDR templates 326 from premature cutting by restriction enzymes because some restriction enzymes do not cut methylated DNA. Other nucleases such as Cas9 may also be prevented from cutting by methylation of a cutting region or PAM recognition site. DNA methylation is a process by which methyl groups are added to the DNA molecule. Methylation can change the activity of a DNA segment without changing the sequence. Two of DNA's four bases, cytosine and adenine, can be methylated. A methylase is an enzyme that recognizes a specific sequence and methylates one of the bases in or near that sequence. Methylation may be controlled by epigenetic editing using a targeting device that is a sequence-specific DNA binding domain which can be redesigned to recognize desired sequences. The targeting device may be fused to an effector domain, which can modify the epigenetic state of the targeted locus. Techniques for using epigenetic editing will be understood by one of ordinary skill in the art. Epigenome manipulations are described in Park, et al., *The epigenome: the next substrate for engineering.* 17 Genome Biology 183 (2016). HDR templates 326 made of RNA may also be modified by methylation. Methylation of RNA is described in S. Lin and R. Gregory, *Methyltransferases modulate RNA stability in embryonic stem cells,* 16(2) Nature Cell Biology 129 (2014).

In one implementation, the HDR template 326 is a ssDNA sequence complementary to the ssRNA sequence 320. The ssDNA sequence may be created by reverse transcriptase (RT) reading the ssRNA sequence 322 and synthesizing a complementary ssDNA sequence. RT is an enzyme used to generate cDNA from an RNA template, a process termed reverse transcription. RT is widely used in the laboratory to convert RNA to DNA for use in procedures such as molecular cloning, RNA sequencing, polymerase chain reaction (PCR), and genome analysis. RT enzymes are widely available from multiple commercial sources. Procedures for use of RT is well known to those of ordinary skill in the art.

A 3'-end sequence 330 and a 5'-end sequence 332 of the HDR template 326 are homologous to one strand of the dsDNA molecule 302 over at least a portion of the first target site 304. The HDR template 326, in both ssDNA and ssRNA implementations, includes a middle portion 334 that, when incorporated into the dsDNA molecule 302, acts as a log of a condition detected the cell 300, represents a unit of arbitrary information such as a binary digit, or stores a different kind of information. In an implementation, the middle portion 334 also introduces another target site. As discussed below, introducing a new target site by insertion of a HDR template 326 can place the cell 300 into a particular state for functioning as a state machine.

Enzyme 306 is illustrated here as a CRISPR/Cas complex with gRNA 308. Other types of enzymes may be used instead of the CRISPR/Cas complex. The single-stranded tail of the gRNA 308 may be extended with a sequence complementary to all or part of the HDR template 326. The HDR template 326 may partially hybridize to the tail of the gRNA 308 forming a double-stranded region. Thus, the molecule 336 may be the HDR template 326. This brings a copy of the HDR template 326 into close physical proximity with the location of the DSB created by the CRISPR/Cas complex which can increase HDR efficiency.

The extended tail of the gRNA 308 may also be designed so that it matches the binding domain of a transcription activator-like effector (TALE) protein. The TALE protein may also have a binding domain complementary to the HDR template 326. This will also bring the HDR template into close proximity with the location of the DSB. The tail of the gRNA 308 may be extended to create regions for attachment of multiple copies of the HDR template 326 or multiple TALE proteins.

TALE proteins are proteins secreted by *Xanthomonas* bacteria via their type III secretion system when the bacteria infect various plant species. These proteins can bind promoter sequences in the host plant and activate the expression of plant genes that aid bacterial infection. They recognize plant DNA sequences through a central repeat domain consisting of a variable number of about 34 amino acid repeats. There appears to be a one-to-one correspondence between the identity of two amino acids in each repeat and each DNA base in the target site. The most distinctive characteristic of TAL effectors is a central repeat domain containing between 1.5 and 33.5 repeats that are usually 34 amino acids in length (the C-terminal repeat is generally shorter and referred to as a "half repeat"). A typical repeat sequence may be shared across many TALE proteins but the residues at the $12^{th}$ and $13^{th}$ positions are hypervariable (these two amino acids are also known as the repeat variable diresidue or RVD). This simple correspondence between amino acids in TAL effectors and DNA bases in their target sites makes them useful for protein engineering applications.

Subsequent to creation of a DSB in the target site 304, the molecule 336 that has hybridized to the tail of the gRNA 308 may be released. In some implementations, introduction of a nucleotide sequence complementary to the tail of the gRNA 308 or binding domain of the TALE protein may compete with the attached molecule 336 and cause disassociation of the HDR template 326, TALE protein, or other molecule. This competition may cause the HDR template 326 to become available for binding to the dsDNA molecule 302 on either side of the DSB.

The cell 300 may also include one or more engineered signaling pathways 338. As used herein, "engineered signaling pathway" includes any pathway in which at least one portion of the pathway is intentionally modified with molecular biology techniques to be different from the wild type pathway and a signal (intracellular or extracellular) causes a change in a rate of transcription of a gene. The engineered signaling pathway 338 may induce a promoter such as the promoter 316 described above. The engineered signaling pathway 338 may also cause a transcription factor to bind to an operator such as the operator 318 described above and prevent transcription. In one implementation, the gene affected by the engineered signaling pathway 338 may be the operon 314 that encodes for the ssRNA sequence 320. Thus, the engineered signaling pathway 338 may function to control an amount of the HDR template 326 available in the cell 300. In one implementation, the gene affected by the engineered signaling pathway 338 may encode for an enzyme that creates DSBs in dsDNA such as enzyme 306. Thus, the number of enzymes which create DSBs in the target sites 304 may be regulated by the engineered signaling pathway 338. The engineered signaling pathway 338 may control the transcription of genes that encode other proteins associated with HDR.

In one implementation, the external receptor 340 may be a G protein-coupled receptor (GPCR). GPCRs constitute a large protein family of receptors, that sense molecules outside the membrane 342 and activate a signaling cascade and, ultimately, cellular responses. The GPCR is activated by an external signal in the form of a ligand or other signal mediator. This creates a conformational change in the GPCR, causing activation of a G protein. Further effect depends on the type of G protein. G proteins are subsequently inactivated by GTPase activating proteins, known as RGS proteins. The ligands that bind and activate these GPCRs include light-sensitive compounds, odors, pheromones, hormones, neurotransmitters, etc. and vary in size from small molecules to peptides to large proteins. When a ligand binds to the GPCR it causes a conformational change in the GPCR, which allows it to act as a guanine nucleotide exchange factor (GEF). The GPCR can then activate an associated G protein by exchanging its bound GDP for a GTP. The G protein's a subunit, together with the bound GTP, can then dissociate from the β and γ subunits to further affect intracellular signaling proteins or target functional proteins directly depending on the a subunit type.

In one implementation, the external receptor 340 may be a photosensitive membrane protein. Photoreceptor proteins are light-sensitive proteins involved in the sensing and response to light in a variety of organisms. Photoreceptor proteins typically consist of a protein moiety and a non-protein photopigment that reacts to light via photoisomerization or photoreduction, thus initiating a change of the receptor protein that triggers a signaling cascade. Pigments found in photoreceptors include retinal (retinylidene proteins, for example rhodopsin in animals), flavin (flavoproteins, for example cryptochrome in plants and animals) and bilin (biliproteins, for example phytochrome in plants). One example of engineered use of light-sensitive proteins is found in Tamsir, A. et al., *Robust Multicellular Computing Using Genetically Encoded NOR Gates and Chemical 'Wires'*, 469 Nature 214 (2011).

The external receptor 340, in some implementations, may be a membrane-bound immunoglobulin (mlg). A membrane-bound immunoglobulin is the membrane-bound form of an antibody. Membrane-bound immunoglobulins are composed of surface-bound IgD or IgM antibodies and associated Ig-α and Ig-β heterodimers, which are capable of signal transduction through a signaling cascade in response to activation by an antigen.

In one implementation, the external receptor 340 may be a Notch protein. The Notch protein spans the cell membrane, with part of it inside and part outside. Ligand proteins binding to the extracellular domain induce proteolytic cleavage and release of the intracellular domain, which enters the cell to modify gene expression. The external receptor 340 may be triggered via direct cell-to-cell contact, in which the transmembrane proteins of the cells in direct contact form the ligands that bind the notch receptor. Signals generated by the Notch protein may be carried to an operon by the Notch cascade which consists of Notch and Notch ligands as well as intracellular proteins transmitting the notch signal.

In one implementation, temperature may activate the signaling pathway 338. Temperature sensing molecules that occur naturally in single-celled organisms include heat shock proteins and certain RNA regulatory molecules, such as riboswitches. Heat shock proteins are proteins that are involved in the cellular response to stress. One example of a heat shock protein that responds to temperature is the bacterial protein DnaK. Temperatures elevated above normal physiological range can cause DnaK expression to become up-regulated. DnaK and other heat shock proteins can be utilized for engineered pathways that respond to temperature. Riboswitches are a type of RNA molecule that can respond to temperature in order to regulate protein translation. An example of a temperature-regulated engineered pathway that has utilized a riboswitch can be found in Neupert, J. et al., *Design of simple synthetic RNA thermometers for temperature-controlled gene expression in Escherichia coli.,* 36(19) Nucleic Acids Res., e124, (2008). Another example of a temperature-sensitive molecule that can be utilized to regulate engineered cell pathways is a temperature-sensitive mutant protein. Single mutations can be made to proteins, which cause the proteins to become unstable at high temperatures, yet remain functional at lower temperatures. Methods for synthesizing temperature-sensitive mutant proteins can be found in Ben-Aroya, S. et al., *Making Temperature-Sensitive Mutants,* 470 Methods Enzymology 181 (2010). An example of a temperature-controlled engineered pathway that utilizes a temperature-sensitive mutant can be found in Hussain, F. et al., *Engineered temperature compensation in a synthetic genetic clock,* 111(3) PNAS 972 (2014).

In one implementation, ion concentration or pH may activate the signaling pathway 338. Examples of cellular sensing molecular mechanisms that detect ionic strength or pH include many viral proteins, such as herpes simplex virus gB, rubella virus envelope protein, influenza hemagglutinin, and vesicular stomatitis virus glycoprotein. An example of a natural cellular pathway that is regulated by pH is penicillin production by *Aspergillus nidulans* as described in Espeso, E. et al., *pH Regulation is a Major Determinant in Expression of a Fungal Penicillin Biosynthetic Gene,* 12(10) EMBO J. 3947 (1993). Another example of a pH-sensitive molecule that can be utilized to regulate engineered cell pathways is a pH-sensitive mutant protein. Single mutations can be made to proteins, which can cause the proteins to become less stable in either acidic or basic conditions. For example, pH-sensitive antibodies can bind to an antigen at an optimal pH but are unable to bind to an antigen at a non-optimal pH. A technique for creating pH-sensitive antibodies that can be used for engineered signaling pathways can be found in Schroter, C. et al., *A generic approach to engineer antibody pH-switches using combinatorial histidine scanning libraries and yeast display,* 7(1) MAbs 138 (2015).

The cell 300 may include multiple different engineered signaling pathways 338 each responding to a unique signal and each promoting or repressing expression of genes responsible for the creation of the HDR templates 326, enzymes 306, or addition of new cut sites into dsDNA that establish a state for the cell 300. Thus, intracellular or extracellular signals may be used to vary the levels of HDR templates 326 or enzymes 306 in the cell 300 thereby changing which target sites 304 are cut and which sequences are used to repair DSBs through HDR. Responding by up or down regulating any of multiple promoters or operators allows the cell 300 to record a log in its DNA of events and complex interactions of events sensed by engineered signaling pathways or the record arbitrary information such as binary digits. In one implementation, the engineered signaling pathway 338 may include an external receptor 340 that can detect extracellular signals across a membrane 342. The membrane 342 may be a cell wall, lipid bilayer, artificial cell wall, or synthetic membrane.

In an implementation, the dsDNA molecule 302 may include genes that encode the components used for modifying existing dsDNA by insertion of HDR templates. In an implementation, the dsDNA molecule 302 may include any or all of a gene encoding an HDR template 326, a gene encoding an enzyme 306 configured to make DSBs, and a gene that encodes a tracking molecule (e.g., RNA, DNA, or protein) for monitoring "state" as described below. An operon that includes all these genes may be added to a cell-free system on a circular dsDNA molecule 302 that also includes the target site 304 to provide complete instructions and molecular machinery for implementing a state machine.

State Machines

Figure 4:
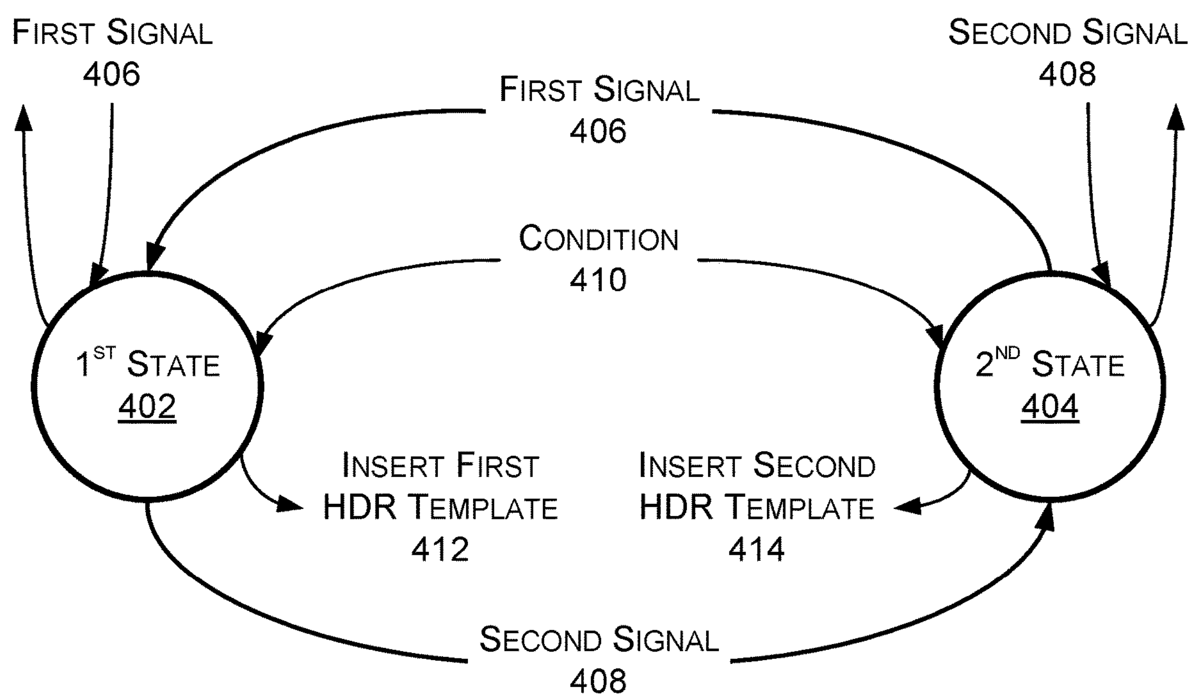
FIG. 4 shows an illustrative state machine.

FIG. 4 shows a representation of a state machine 400 implemented in part by regulating the insertion of HDR templates. A state machine is a mathematical model of computation. A state machine can be in one of a finite number of states at any given time. State machines can change from one state to another in response to some external inputs; the change from one state to another is called a transition. A state machine may be described by a list of its states, its initial state, and the conditions for each transition.

In the state machine 400 of FIG. 4, HDR templates are inserted into existing double-stranded polynucleotides of a cell according to the techniques described above. In this simple representation, the cell is always in one of two states: $1^{st}$ state 402 or $2^{nd}$ state 404 but state machines having a greater number of states will operate according to the same principles and are encompassed within the scope of this disclosure. The states may be implemented in any number of ways such as activating (or silencing) promoters or other regulatory elements, increasing or decreasing the concentration (or activity) of nucleases that create DSBs at specific sites, or making specific cut sites available through insertion of HDR templates that include cut sites. When the state information is directly stored in a polynucleotide this ensures that the state is maintained stably. The states and transitions between states may also be regulated by existing cellular transitions. Examples include the cell cycle and checkpoints for cell differentiation in development. Thus, the concept of "state" from the mathematical model is represented in a cell by the presence of a specific molecule, a polynucleotide sequence, or other physical modification.

The cell cycle or cell-division cycle, for example, is the series of events that take place in a cell leading to its division and duplication of its DNA (DNA replication) to produce two daughter cells. In bacteria, which lack a cell nucleus, the cell cycle is divided into the B, C, and D periods. The B period extends from the end of cell division to the beginning of DNA replication. DNA replication occurs during the C period. The D period refers to the stage between the end of DNA replication and the splitting of the bacterial cell into two daughter cells. In cells with a nucleus, as in eukaryotes, the cell cycle is also divided into three periods: interphase, the mitotic (M) phase, and cytokinesis. During interphase, the cell grows, accumulating nutrients needed for mitosis, preparing it for cell division and duplicating its DNA. During the mitotic phase, the chromosomes separate. During the final stage, cytokinesis, the chromosomes and cytoplasm separate into two new daughter cells. To ensure the proper division of the cell, there are control mechanisms known as cell cycle checkpoints.

Two key classes of regulatory molecules, cyclins and cyclin-dependent kinases (CDKs), determine a cell's progress through the cell cycle. Cyclins form the regulatory subunits and CDKs the catalytic subunits of an activated heterodimer; cyclins have no catalytic activity and CDKs are inactive in the absence of a partner cyclin. When activated by a bound cyclin, CDKs perform a common biochemical reaction called phosphorylation that activates or inactivates target proteins to orchestrate coordinated entry into the next phase of the cell cycle. Different cyclin-CDK combinations determine the downstream proteins targeted. CDKs are constitutively expressed in cells whereas cyclins are synthesized at specific stages of the cell cycle, in response to various molecular signals.

Two families of genes, the cip/kip (CDK interacting protein/Kinase inhibitory protein) family and the INK4a/ARF (Inhibitor of Kinase 4/Alternative Reading Frame) family, prevent the progression of the cell cycle. Because these genes are instrumental in prevention of tumor formation, they are known as tumor suppressors.

The cip/kip family includes the genes p21, p27 and p57. They halt cell cycle in G1 phase, by binding to, and inactivating, cyclin-CDK complexes. p21 is activated by p53 (which, in turn, is triggered by DNA damage e.g. due to radiation). p27 is activated by Transforming Growth Factor of β (TGF β), a growth inhibitor. The INK4a/ARF family includes p16INK4a, which binds to CDK4 and arrests the cell cycle in G1 phase, and p14ARF which prevents p53 degradation. Any of the regulatory molecules involved in the cell cycle may be used, for example by an engineered signaling pathway, to control an HDR template and associated homology directed repair behavior in order to create a genetic record that tracks the timing of the corresponding natural cellular cycle.

A first signal 406 changes a cell in the $2^{nd}$ state 404 into the $1^{st}$ state 402. The first signal 406 may be a type of signal that can be generated by manipulating the cell or its environment such as a change in temperature, change in light levels, introduction of a chemical, etc. The first signal 406 may also be a regulatory molecule such as a cyclin or CDK. Checkpoints for regulating cellular differentiation in development may also be used to transition between states. Similarly, a second signal 408 changes the cell from the $1^{st}$ state 402 into the $2^{nd}$ state 404. Once a cell is in a given state, tracking molecules in the cell may function to maintain the state. The tracking molecules may be such things as transcription factors that regulate the behavior of gene regulatory elements. The regulated gene may encode a component used in HDR such as an HDR template or enzyme used to create DSBs. For example, a first transcription factor may be present when the cell is in the $1^{st}$ state 402 and a second, different transcription factor may be present when the cell is in the $2^{nd}$ state 404. The concentration of tracking molecules may decrease with time due to degradation (e.g., by nucleases). Once the level of a tracking molecule drops below a functional level, the cell may transition to a different state or enter an undefined state in which the cell does not behave according to any of the established states. The functional level of a tracking molecule is the amount of that tracking molecule needed to maintain a state or to convert a cell to a state.

The tracking molecule may be a protein such as an enzyme that creates DSBs at specific locations. Proteins such as Cas9 will degrade in cells due to the presence of proteases. Thus, a state that depends on presence of a protein for maintenance of the state will last so long as the concentration of the protein is maintained. The rate of degradation of a protein may be experimentally established for a given cellular system. The stability of a protein can be altered by introducing mutations into the amino acid sequence that make the protein more or less resistant to denaturation or proteolytic degradation. Persons having ordinary skill in the art will appreciate various techniques to modify the duration that a protein remains active in a given cellular environment. Techniques such as directed evolution, DNA shuffling and two-hybrid screening are known in the art and may be used to rapidly screen large numbers of mutant proteins for the desired stability characteristics. In addition, protein degradation rate may be altered by attaching a short, organism-specific, oligonucleotide sequence to the 3'-end of the gene which encodes the protein as described in Andersen et al. (1998) Appl. Environ. Microbiol. 64:2240-2246. This sequence targets the encoded protein for rapid degradation by the cell which can shorten the time that the cell stays in a given state.

Tracking molecules may also be RNA that makes HDR templates available for modifying existing double-stranded polynucleotides or gRNA for guiding Cas nucleases to specific target sites. Like proteins RNA also degrades. The rate of this degradation can be modified somewhat leading to longer or shorter periods of a cell being in a given state when that state depends on the availability of an RNA product. After export to the cytoplasm, mRNA (including gRNA) is protected from degradation by a 5' cap structure and a 3' poly(A) tail. The rate of mRNA degradation is typically minutes in prokaryotes and hours-months in eukaryotes. A rate of degradation of the RNA may be determined in part by a modification to a 3' poly(A) tail. A longer poly(A) tail generally correlates with greater stability of RNA and a shorter poly(A) tail generally leads to faster degradation of the RNA. Specifically, the degradation of RNA may be affected by the 3'-untranslated region (3'-UTR). The 3'-UTR can influence polyadenylation, translation efficiency, localization, and stability of the mRNA. The 3'-UTR contains both binding sites for regulatory proteins as well as microRNAs (miRNAs). By binding to specific sites within the 3'-UTR, miRNAs can decrease gene expression of various mRNAs by either inhibiting translation or directly causing degradation of the transcript. The 3'-UTR contains both binding sites for regulatory proteins as well as miRNAs. By binding to specific sites within the 3'-UTR, miRNAs can decrease gene expression of various mRNAs by either inhibiting translation or directly causing degradation of the transcript.

Mature microRNAs (miRNAs) are a class of naturally occurring, small non-coding RNA molecules, about 21-25 nt in length. They are found in plants, animals and some viruses, and have functions in RNA silencing and post-transcriptional regulation of gene expression. MicroRNAs are partially complementary to one or more messenger RNA (mRNA) molecules, and their main function is to down-regulate gene expression in a variety of manners, including translational repression, mRNA cleavage, and deadenylation.

Encoded by eukaryotic nuclear DNA in plants and animals and by viral DNA in certain viruses whose genome is based on DNA, miRNAs function via base-pairing with complementary sequences within mRNA molecules. As a result, the RNA can be silenced, by one or more of the following processes: cleavage of the RNA strand into two pieces, destabilization of the RNA through shortening of its poly(A) tail, and less efficient translation of the RNA into proteins by ribosomes. For example, miR16 contains a sequence complementary to the AU-rich element found in the 3'-UTR of many unstable mRNAs, such as TNF alpha or GM-CSF. It has been demonstrated that given complete complementarity between the miRNA and target mRNA sequence, Ago2 can cleave the mRNA and lead to direct mRNA degradation. Jing, Q. et al. *Involvement of microRNA in AU-rich element-mediated mRNA instability.* 120(5) Cell 623 (2005).

The genes encoding miRNAs are much longer than the processed mature miRNA molecule. Many miRNAs are known to reside in introns of their pre-mRNA host genes and share their regulatory elements, primary transcript, and have a similar expression profile. MicroRNAs are transcribed by RNA polymerase II as large RNA precursors called pri-miRNAs and comprise of a 5' cap and poly-A tail. The pri-miRNAs are processed in the nucleus by the microprocessor complex, consisting of the RNase III enzyme Drosha, and the double-stranded-RNA-binding protein, Pasha/DGCR85. The resulting pre-miRNAs are approximately 70-nt in length and are folded into imperfect stem-loop structures. The pre-miRNAs are then exported into the cytoplasm by the karyopherin exportin 5 (Exp5) and Ran-GTP complex. Ran (ras-related nuclear protein) is a small GTP binding protein belonging to the RAS superfamily that is essential for the translocation of RNA and proteins through the nuclear pore complex. The Ran GTPase binds Exp5 and forms a nuclear heterotrimer with pre-miRNAs. Once in the cytoplasm, the pre-miRNAs undergo an additional processing step by the RNAse III enzyme Dicer generating the miRNA, a double-stranded RNA approximately 22 nt in length.

The input that changes a cell from one state to another (e.g., first signal 406, second signal 408) may be a combination of multiple inputs. For example, the transition from the 1$^{st}$ state 402 to the 2$^{nd}$ state 404 may be triggered by the presence of two chemicals, by the combination of two factors such as salinity and pH, etc. Thus, presence of a cell in a state may be an indication that a combination of two, or more, inputs were all present.

When a cell is in the 1$^{st}$ state 402, the first signal 406 will not change the state of the cell. The cell will remain in the 1$^{st}$ state. For example, if an inducible promoter is activated by the first signal 406, then additional exposure to the first signal 406 will not change the behavior of the cell because the inducible promoter is already active. If the Pt state is maintained by a tracking molecule that decreases in concentration over time, additional exposure to the first signal 406 may cause an increase in the concentration of the tracking molecule leading to prolonging the 1$^{st}$ state 402. The cell will response similarly to exposure to the second signal 408 while the cell is in the 2$^{nd}$ state 404. In an implementation, one of the states (e.g., the 1$^{st}$ state 402) may be a default state that the cell returns to if other states (e.g., the 2$^{nd}$ state 404) are not maintained. One way of constructing a cell to have this behavior is by placing a gene responsible for the 1$^{st}$ state 402 under the control of a constitutive promoter and by placing a gene responsible for the 2$^{nd}$ state 404 under the control of an inducible promoter. The cell may be further configured so that activation of the inducible promoter represses activity of the constitutive promoter or that otherwise moves the cell out of the 1$^{st}$ state 402 when the cell enters the 2$^{nd}$ state 404. Thus, in this type of configuration activation of the inducible promoter transitions the cell to the 2$^{nd}$ state 404 and lack of activation of the inducible promoter keeps the cell in the 1$^{st}$ state 402. Techniques for designing genetic systems under the control of specific promoters are well known to those having ordinary skill in the art and any suitable technique may be used or adapted to control the activities of a cell when in a particular state.

Molecular switches such as bi-stable and tri-stable switches may be used to establish a state and change between states. Techniques for creating and using bi-stable molecular switches are described in Gardner, T. S. et al., *Construction of a genetic toggle switch in Escherichia coli.* 403 Nature 339 (2000) and Lebar, T. et al., *A bistable genetic switch based on designable DNA-binding domains.* 5 Nature Communications 5007 (2014).

The state machine 400 responds differently to the same condition 410 depending on its current state. The condition 410 may be receipt of a signal indicating a molecular signal, a binary digit, or something else. The condition 410 may also be the presence of a molecule in the cell such as an enzyme, a HDR template, a double-stranded polynucleotide or another molecule. Ultimately the difference in state leads to a different HDR template being inserted into a double-stranded polynucleotide. When the condition 410 is present in a cell in the 1$^{st}$ state 402, the cell will insert a first HDR template 412 into a double-stranded polynucleotide. When the condition 410 is present in the cell in the 2$^{nd}$ state 404, the cell will insert a second HDR template 414 into a double-stranded polynucleotide. The cell may be configured to insert first HDR template 412 and the second HDR template 414 into the same double-stranded polynucleotide or into different double-stranded polynucleotides. If the cell is capable of being in an undefined state that is neither the 1$^{st}$ state 402 nor the 2$^{nd}$ state 404 then presence of the condition 410 will not result in insertion of either the first HDR template 412 or the second HDR template 414. The undefined state could be characterized by the lack of insertion of any HDR template.

A cell may include multiple state machines that function wholly orthogonal to each other with distinct states and transitions. The tracking molecules, signals, and other molecular triggers of state can be different as between two orthogonal state machines. More complex and inter-connected state machines are also possible such as two state machines both responding to the same signal by transitioning between states.

Figure 5:
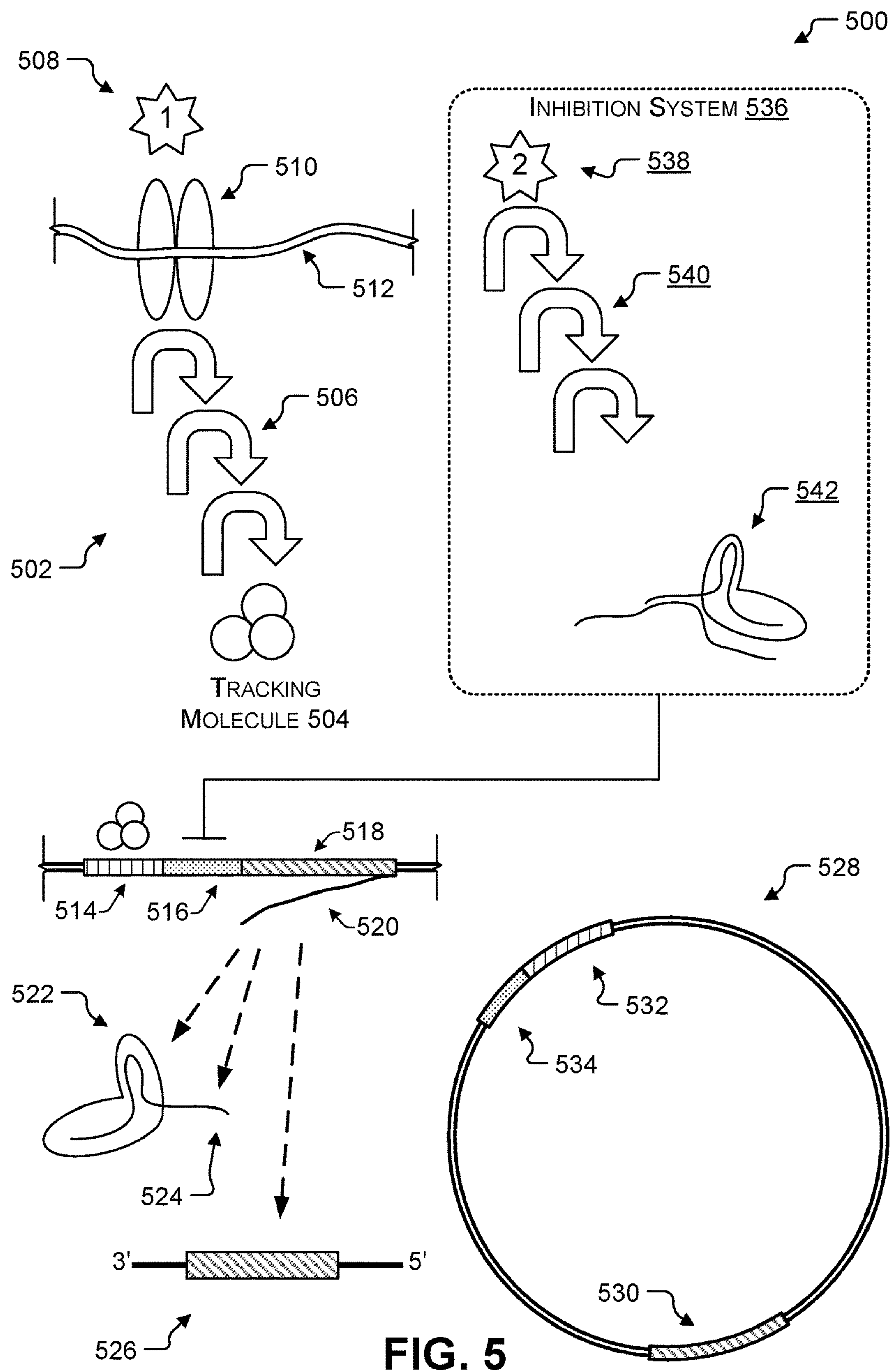
FIG. 5 shows a schematic representation of illustrative components in a molecular state machine.

FIG. 5 shows a cell 500 that includes components of a molecular state machine. Some of the components of the cell 500 may be the same or similar to the components introduced in the description of the cell 300 in FIG. 3. The molecular state machine can include a signaling pathway 502. The signaling pathway 502 may be an engineered signaling pathway that is created or modified in some way to be different from a wild-type signaling pathway. This signaling pathway 502 may be the same or similar to the signaling pathway 338 in FIG. 3. The signaling pathway 502 controls the availability of a tracking molecule 504. The tracking molecule 504 "keeps track" of the state of the cell 500 by establishing or maintaining a state. In an implementation, the tracking molecule may be a transcription factor.

The signaling pathway 502 may include a signaling cascade 506 that carries a signal from a first messenger (i.e., the initial signal) and eventually results in increasing or decreasing a concentration of the tracking molecule 504. The signaling pathway 502 may respond to ionic concentration; placing a cell in a different ionic environment or altering pH surrounding the cell may thus be used to control the availability of the tracking molecule 504. Similarly, temperature may control behavior the signaling pathway 502. Thus, by altering the temperature, the concentration of the tracking molecule 504 may be increased or decreased.

An initial signal 508 that sets the signaling cascade 506 into action may be an internal or external signal. In an implementation, the initial signal 508 may be the first signal 406 or the second signal 408 of FIG. 4. The signaling pathway 502 may be a trans-membrane signaling pathway that includes an external receptor 510 which detects extracellular signals and communicates the signals across a membrane 512. The external receptor 510 and the membrane 512 may be the same or similar to the external receptor 340 and the membrane 342 shown in FIG. 3. These and other similar sensing mechanisms may be engineered to affect the availability of the tracking molecule 504.

The tracking molecule 504 may interact with a promoter 514 or other regulatory element such as an operator 516 to control transcription of a gene 518. The sequence of the promoter region controls the binding of the RNA polymerase and transcription factors. An operator 516 is a segment of DNA to which a repressor binds to decrease or stop gene expression. The promoter 514, operator 516, and gene 518 may be included in an operon. An operon is a contiguous region of DNA that includes cis-regulatory regions (e.g., repressors, promoters) and the coding regions for one or more genes or functional mRNAs (e.g., siRNA, tracrRNA, gRNA, shRNA, etc.).

A "transcription factor" is a protein that binds near the beginning of the coding sequence (transcription start site) for a gene or functional mRNA. Transcription factors are necessary for recruiting DNA polymerase to transcribe DNA. A transcription factor can function as a repressor, which can bind to the operator 516 to prevent transcription. The gene 518, the promoter 514, and the operator 516 are on a dsDNA molecule that may be genomic DNA of a cell or other DNA such as a plasmid or vector. In some implementations, the promoter 514 may respond to signals such as temperature or pH, and thus, the promotor 514 itself may be the signaling pathway 502.

The gene 518 encodes for a RNA product 520. Thus, a rate of transcription of the RNA product can change based on availability of the tracking molecule 504. The RNA product 520 may be translated into protein, used directly as RNA, or reverse transcribed into DNA. In one implementation, the RNA product 520 may be mRNA that encodes for a nuclease 522 that creates DSBs such as, for example, enzyme 104 shown in FIG. 1, enzyme 200 shown in FIG. 2, or enzyme 306 shown in FIG. 3. The nuclease 522 may be, for example, any of the Cas enzymes described in this disclosure.

In one implementation, the RNA product 520 encodes for gRNA 524 that is used by the Cas enzyme to target a specific DNA sequence. The system may be designed to have all components needed for performing HDR other than the gRNA 524. Thus, transcription of the gRNA 524 in response to the tracking molecule 504 can provide the last component needed to perform HDR and result in incorporation of an HDR template.

In one implementation, the RNA product 520 may itself be or may encode for an HDR template 526. The HDR template 526 may be, for example, the HDR template 108 shown FIG. 1, the HDR template 204 shown in FIG. 2, or the HDR template 326 shown in FIG. 3. The RNA product 520, although it is ssRNA, may be capable of functioning as an HDR template 526 due to the ability of RNA to hybridize with DNA. RNA transcript-mediated HDR has been shown to function successfully in eukaryotic cells. See Keskin, H. et al., *Transcript-RNA-templated DNA recombination and repair,* 515 Nature 436 (2014) and Storici, F. et al., *RNA-templated DNA repair,* 447 Nature 338 (2007). If RNA is used as the HDR template, the cell may be further modified to reduce or remove enzymes that degrade RNA-DNA hybrids. In one implementation, the cell using RNA as the HDR template may be *S. cerevisiae*. Additionally, complementary DNA (cDNA), resulting from reverse-transcription of mRNA, and/or transcript RNA itself may aid DSB repair via HDR. Moreover, splicing of both expressed RNA and potentially of mRNA can change the sequence of RNA that serves as a template for reverse transcriptase to synthesize cDNA. Thus, the cDNA used as an HDR template may have a different sequence, due to splicing, than genomic or other DNA encoding the initial RNA transcript. The RNA product 520 may also be converted to ssDNA by reverse transcriptase and used as the HDR template 526 in the form of DNA.

The cell 500 can also include a double-stranded polynucleotide 528 having a target site 530. The double-stranded polynucleotide 528 may be the same or similar to the dsDNA molecule 302 shown in FIG. 3. The target site 530 may be the same or similar to target sites 102, 114, 116, 210, 218, or 304 shown in FIGS. 1, 2, and 3. The double-stranded polynucleotide 528 may be genomic DNA, a vector, or plasmid introduced to the cell 500 by any suitable method.

The current "state" can represent the sequence present in the double-stranded polynucleotide 528 at the time a given DSB is created. The state may represent which target site 530 is available for cutting by a nuclease 522. For example, a target site 530 on a double-stranded polynucleotide 528 may be capable of being cut only by a specific type of nuclease 522 (e.g., $X_1X_2$, $Y_1Y_2$, $Z_1Z_2$ represent target sites that are cut by different enzymes). Integration of a different target site by addition of an HDR template 526 into a cut site of an existing target site 530 may change the available target site (e.g., integration of $X_1Y_1Y_2X_2$ into $X_1X_2$ changes the available target site from $X_1X_2$ to $Y_1Y_2$). If the cell 500 only includes the target site $Z_1Z_2$, for example, synthesis of nuclease 522 configured to cut the target site $Y_1Y_2$ would not be immediately useful for HDR. Accordingly, state may be used to suppress the transcription of certain genes.

Current state may be recorded biochemically by using a genetically designed bi-stable switch. With one or more bi-stable switches, the current state may be recorded biochemically by creating molecular records based on which enzyme and/or HDR template was used last through a positive feedback loop. In some implementations, genes encoding multiple enzymes and multiple HDR templates may also be present in the cell 500 and each of the genes may be regulated by specific, and known promoters 514. The genes that encode for a given enzyme and accompany regulatory elements may be included in one or more operons. Activation of the genes by upregulation or cessation of suppression, may increase the amount of the desired enzyme and/or HDR template. This may also generate tracking molecules 504 that can be used to monitor state. The tracking molecules 504 may also be encoded by the same or different operons.

The current level of a tracking molecule 504 can serve as an on/off regulation signal for a gene encoding a given operon. In a system with a bi-stable repressor, the repressor has two states 0/1, which are flipped after each operation. For example, after the HDR template $X_1Y_1Y_2X_2$ is used (e.g., as identified by the concentration becoming greater than a threshold level) an associated tracking molecule 504 may set the state of the bi-stable repressor. Continuing with this example, each HDR template may be associated with a different bi-stable repressor and at any given time all but one of the bi-stable repressors may be in a state associated with "off" and one may be in a state associated with "on." Thus, by examination of the state of multiple bi-stable repressors it is possible to identify which HDR template was last used. A similar mechanism may keep track of which enzyme was last used. A person having ordinary skill in the art will know how to create a bi-stable switch using proteins that serve as transcription factors or repressors having DNA-binding domains.

To avoid potential interference by molecules remaining from an earlier iteration, flipping of the bi-stable repressor may be handled as a multistage process that first pauses until editing of the double-stranded polynucleotide 528 has stopped, then switches the state of the repressor using a temporally decaying signal indicating which state the repressor should change to. The temporally decaying signal is initiated during the active stage of the last iteration. Once the signal has decayed below a threshold level and the repressor has fully switched into the new state, operons regulating molecules used for the next iteration are unblocked. The operon that lacks the repressor appropriately corresponding to the current state and has a promoter for the current input signal is then able to proceed to transcribe.

Appropriate DNA segments 532 may be inserted into a vector by a variety of procedures. In general, DNA segments 532 may be inserted into an appropriate restriction endonuclease site(s) by procedures known in the art, which may be performed without undue experimentation by a skilled artisan. A DNA segment 532 in an expression vector may be operatively linked to an appropriate expression control sequence(s) (i.e., a promoter 534) to direct synthesis. The DNA segment 532 may encode an HDR template, an mRNA for a nuclease, a gRNA that functions with a Cas enzyme, or something else. The double-stranded polynucleotide 528 may provide both a target site 530 for recording molecular events or arbitrary information and genes that provide the molecular components used by the cell 500.

An inhibition system 536 may be present in the cell 500. The inhibition system 536 can reduce or stop the amount of HDR that occurs by reducing the amount of HDR template available in the cell, by reducing the activity of a nuclease that creates DSBs at cut site in the target site 530, or by otherwise inhibiting the HDR process. The inhibition system 536 may cause state transitions by inhibiting the function of the gene 518 when the cell 500 shifts to a different state. A second signal 538 associated with a second state may activate a signaling cascade 540 that results in inhibition of gene expression such as by generating a repressor protein that binds to the operator 516 or to another regulatory element such as a silencer. The second signal 538 may also promote the synthesis of HDR templates or nucleases that function when the cell in in the second state. Thus, a state transition may be achieved by responding to a signal by promoting the activity or increasing the availability of HDR components used in a first state while inhibiting the activity or decreasing the availability of HDR components used in another state.

The inhibition system 536 may include a repressor (and/or "knockdown") that can be a protein or mRNA (small hairpin loops (shRNA), interfering mRNA (RNAi or siRNA)) that binds to DNA/RNA and blocks either attachment of the promoter, blocks elongation of the polymerase during transcription, or blocks mRNA from translation. In addition to repressors, the CRISPR/Cas9 system itself may be used for sequence-specific repression of gene expression in prokaryotic and eukaryotic cells. Specifically, the technique of CRISPR interference (CRISPRi) 542 uses catalytically dead Cas9 lacking endonuclease activity to regulate genes in an RNA-guided manner. Catalytically inactive Cas9 may be created by introducing point mutations into the Cas9 protein such as at the two catalytic residues (D10A and H840A) of the gene encoding Cas9. In doing so, dCas9 is unable to cleave dsDNA but retains the ability to target DNA. Targeting specificity for CRISPRi 542 is determined by complementary base pairing of a gRNA to the genomic loci. The gRNA may be designed to target the promoter 514. The complex of the catalytically dead Cas9 and the gRNA will block activation of the promoter 514 and turn off expression of the gene 518.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations may be modified or omitted.

Figure 6:
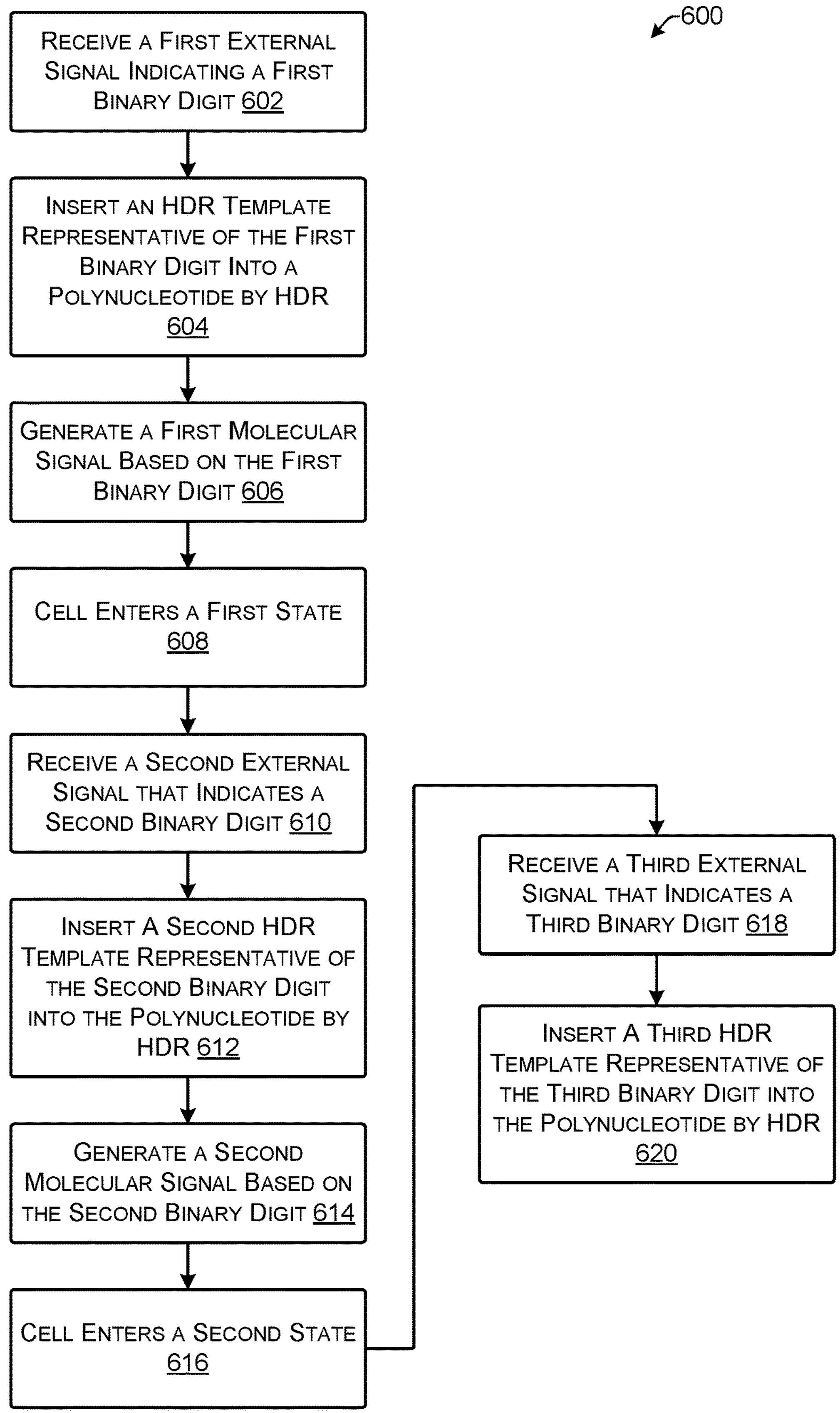
FIG. 6 shows an illustrative process for recording binary digits in a polynucleotide according to a context-dependent code that is implemented through molecular states.

FIG. 6 shows a process 600 of encoding binary data in an existing polynucleotide. Binary data, or other arbitrary information such as data encoded in a scheme other than binary, may be stored in a polynucleotide by controlling the sequence of individual nucleotides. The technique of this disclosure stores data in DNA by repeatedly cutting and inserting a new sequence into the existing DNA. Each insert provides within the insert a target site for the next round of DNA cutting and subsequent insertion. Repeating this process creates a DNA molecule with a series of nested inserts. The order of the nested inserts may be interpreted as encoding a series of 1s and 0s. Use of a context-dependent code prevents adjacent insertions of the same polynucleotide sequence into the double-stranded polynucleotide even when writing a string of the same binary digit (e.g., 000 or 111).

The encoding scheme described herein allows for insertion of DNA sequences representing an unbounded length of bits using only three different target sequences and six different HDR templates as explained below. The three target sequences are represented as $X_1X_2$, $Y_1Y_2$, and $Z_1Z_2$. The first portion of the target sequences (e.g., $X_1$, $Y_1$, or $Z_1$) corresponds to a subsequence 102(A) or subsequence 116(A) as shown in FIG. 1. The remaining portion of the target sequences (e.g., $X_2$, $Y_2$, or $Z_2$) corresponds to subsequence 102(B) or subsequence 116(B) shown in FIG. 1. Thus, each X, Y, and Z represents a DNA sequence of about 5 to 20 nt such as, for example only, ACTGAA, GCCTCAT, TGACG, etc. In some implementations $X_1=X_2$, etc., but in other implementations the first portion of a target sequence may be different in sequence and/or length from the remaining portion of a target sequence.

The HDR templates all have end regions that are homologous to one of the target sequences. Thus, the HDR templates will have sequences of the structure: $X_1\_\_X_2$, $Y_1\_\_Y_2$, and $Z_1\_\_Z_2$. Recall that the middle region of the HDR templates itself encodes a target site. Thus, the middle region for any given HDR template will be one of $X_1X_2$, $Y_1Y_2$, or $Z_1Z_2$. In order to precisely control location of insertion, HDR templates do not encode the target site into which the HDR template is to be inserted. For example, $X_1X_1X_2X_2$ is not a valid HDR template according to this encoding. Thus, if the target sequence is "X" the middle region of the HDR template may encode the target sequence for "Y" or "Z"; if the target sequence is "Y" the middle region may encode "X" or "Z"; if the target sequence is "Z"

the middle region may encode "X" or "Y". This leads to the six HDR templates: $X_1Y_1Y_2X_2$, $X_1Z_1Z_2X_2$, $Y_1X_1X_2Y_2$, $Y_1Z_1Z_2Y_2$, $Z_1X_1X_2Z_2$, and $Z_1Y_1Y_2Z_2$.

A context-dependent encoding using three target sites and six HDR templates is shown in Table 1 below. This is only one possible encoding and other encodings that use a greater number of target sites and HDR templates are also possible. Moreover, it is also possible to use multiple encodings in the same cell or system. For all context-dependent encoding systems the particular HDR template used to encode information depends on the previous information recorded in the polynucleotide.

TABLE 1

Context-dependent binary encoding

| Current State | Repair Template | Encoded Bit |
|---|---|---|
| $X_1X_2$ | $X_1Y_1Y_2X_2$ | 0 |
| $X_1X_2$ | $X_1Z_1Z_2X_2$ | 1 |
| $Y_1Y_2$ | $Y_1X_1X_2Y_2$ | 0 |
| $Y_1Y_2$ | $Y_1Z_1Z_2Y_2$ | 1 |
| $Z_1Z_2$ | $Z_1X_1X_2Z_2$ | 0 |
| $Z_1Z_2$ | $Z_1Y_1Y_2Z_2$ | 1 |

The current state represents the sequence present in the dsDNA at the time a given DSB is created. The current state may be tracked by a tracking molecule or a computer that is provided with a record of the initial target site of the dsDNA and with the sequences of each HDR template as the respective templates are brought into contact with the dsDNA. Thus, by referencing the current state as stored in the computer, the appropriate HDR template can be selected from Table 1 (or similar table for a different encoding) in order to encode the desired next bit.

At 602, a first external signal indicating a first binary digit is received. The first external signal may be a chemical, light, temperature, change in pH, radiation, an antigen, etc. Conditions of the cell may be deliberately modified to cause the cell to record in its genetic material a nucleotide sequence corresponding to the first binary digit. For example, the cell may be heated to record "1" and chilled to record "0." Thus, a sequence of temperature modifications may be used to communicate a string of binary digits to the cell. In one implementation, this may be done by placing the cell in a thermocycler and precisely controlling the temperature of the environment surrounding the cell.

At 604, an HDR template representative of the first binary digit can be inserted into a polynucleotide by HDR. The first HDR template may represent the first binary digit according to a context-dependent code such as, for example, the context-dependent code described above. The first HDR template may include a 3'-end sequence and a 5'-end sequence each encoding a second subsequence that is homologous to the first subsequence in the first target site. Thus, in this implementation the 3'-end sequence and the 5'-end sequence have the same sequence, but in other implementations they may have different sequences. The first HDR template may also include a middle portion that includes two adjacent instances of a third subsequence that forms the next target site after insertion into the double-stranded polynucleotide as shown in FIGS. 1 and 2.

A response to the first external signal may include making sufficient copies of the first HDR template available so that HDR can occur, making a nuclease available, if the nuclease is Cas9, then the first molecular signal may include making targeted gRNA available. The first external signal, no matter how generated, may be detected by an engineered signaling pathway in the cell and this detection may cause the cell to increase transcription of either the first HDR template or an enzyme. Increasing transcription of the first HDR template ultimately results in more copies of the first HDR template being available for incorporation into the double-stranded polynucleotide in the cell. The first HDR template includes a first middle portion that is not homologous to the double-stranded polynucleotide, and thus, represents a new nucleotide sequence that will be inserted by HDR. Similarly, increase in the number of functional enzymes that act at the cut site, increases the number of DSBs that are available to be repaired by the HDR templates. Either, or both, may ultimately result in more copies of the first middle portion of the first HDR template being incorporated into the double-stranded polynucleotide.

The HDR temple may be generated by a gene under control of a regulated promoter that responds to the first external signal. The mRNA gene product may be converted to DNA through use of RT to create a DNA molecule that is the final HDR template. In some implementations, the mRNA may itself serve as the HDR template without conversion to DNA.

In order to limit where the nuclease cuts the double-stranded polynucleotide, the first target site may be unique in the double-stranded polynucleotide at the time of making the first DSB. The first target site may also be unique across a population of double-stranded polynucleotides that is available for the first enzyme to act on. For example, if there are multiple circular dsDNA molecules within a cell, the first target site may exist only once within the entire population of circular dsDNA molecules. Alternatively, the first target site may be unique per dsDNA molecule, but the first enzyme may have access to multiple different dsDNA molecules each including one instance of the first target site. It is understood by persons having ordinary skill in the art that the enzyme (even if referred to in the singular herein) may include a plurality of individual and equivalent enzyme molecules. In some implementations, the first target site may include a first subsequence that is repeated once resulting in a second subsequence that is the same as the first subsequence. For example, if the first subsequence is GTACTA then the second subsequence is the same and the sequence of the target site is (SEQ ID NO: 9)
GTACTAGTACTA.

The enzyme may be any of the illustrative types of enzymes identified in this disclosure such as a restriction enzyme, a homing endonucleases (HE), a CRISPR/Cas system, a TALEN, or a zinc finger.

At 606, a first molecular signal is generated based on the first binary digit. The first molecular signal may be a tracking molecule such as the tracking molecule 504 shown in FIG. 5. As discussed above, the transcription factor can activate a promoter which is associated with establishing or maintaining the first state of the cell. The first molecular signal may also directly or indirectly lead to suppression of cellular activity associated with a different state.

At 608, the cell enters a first state. For example, the first state may be the $1^{st}$ state 402 shown in FIG. 4. Entering the first state may occur simultaneously with ending another state such as a second state.

At 610, the cell receives a second external signal that indicates a second binary digit. The second binary digit may be the same or different that the first binary digit (e.g., 01 or 00).

At 612, a second HDR template is inserted into the double-stranded polynucleotide by HDR. The second HDR template is representative of the second binary digit according to the context-dependent code based on the cell being in the first state. The second HDR template comprises a 3'-end sequence and a 5'-end sequence that are homologous to corresponding portions of a target site on the double-stranded polynucleotide.

Using nomenclature introduced earlier in this disclosure, the first HDR template may be represented as XaXXaX which can be inserted into the target site XX and includes, after insertion, the same target site XX in the middle. While, the second HDR template may be represented as XbXXbX with "b" representing the part of the second middle portion that is different from the first middle portion of the first HDR template (i.e., "a" "b"). Thus, presence of the polynucleotide sequence corresponding to "a" corresponds to a first binary digit and presence of "b" corresponds to a second binary digit. The sequence XaXbXXbXaX can then provide a record of the binary digits. The sequences "a" and "b" both as they exist in HDR templates and following integration into a double-stranded polynucleotide are "identifier regions" that provide identification separate from the polynucleotide sequences used for forming homologies.

The target site that the second HDR template is inserted into may have existed before recording of the binary digits began, or the target site may be introduced by the first HDR template. The second HDR template also includes a middle region that comprises an identifier region that represents the second binary digit and an additional target site. The additional target site has a sequence based on the first state. For example, both XaXXaX and XaYYaX can be HDR templates that represent the same binary digit, but the particular middle region (XX or YY) may depend on the state of the cell.

At 614, a second molecular signal based on the second binary digit is generated. If the second binary digit is different from the first (e.g., 01 or 10) then the second molecular signal can place the cell in to a second state such as the $2^{nd}$ state 404 of FIG. 4 that is different than the first state.

At 616, the cell enters the second state that is different from the first state. The effect of the second state, as described above, may be the availability of different HDR templates for insertion or different enzymes that can create DSBs. Increasing the availability of either may be done by increasing the transcription of genes that directly or indirectly encode HDR templates or enzyme or by decreasing degradation of RNA, DNA, or protein gene products. In an implementation, the first state may be a first stable state of a bi-stable molecular switch and the second state may be a second state of the bi-stable molecular switch.

At 618, a third external signal is received that indicates a third binary digit. The third binary digit may be the same as the second binary digit or different. If the third external digit is the same as the second binary digit then the third external signal may be the same as the second external signal. Similarly, if the third binary digit is the same as the first binary digits, then the third external signal may be the same as the first external signal. Thus, the external signal for "0" and likewise the external signal for "1" are constant and do not vary based on the state of the cell.

At 620, the third HDR template representative of the third binary digit according to the context-dependent code is inserted into the double-stranded polynucleotide by HDR. The specific HDR template used as the third HDR template is based on the cell being in the second state that resulted from recording the second binary digit. Even if all of the three binary digits may be the same (e.g. 000 or 111) but due to the context-dependent code the same HDR template will not be inserted three times.

Figure 7:
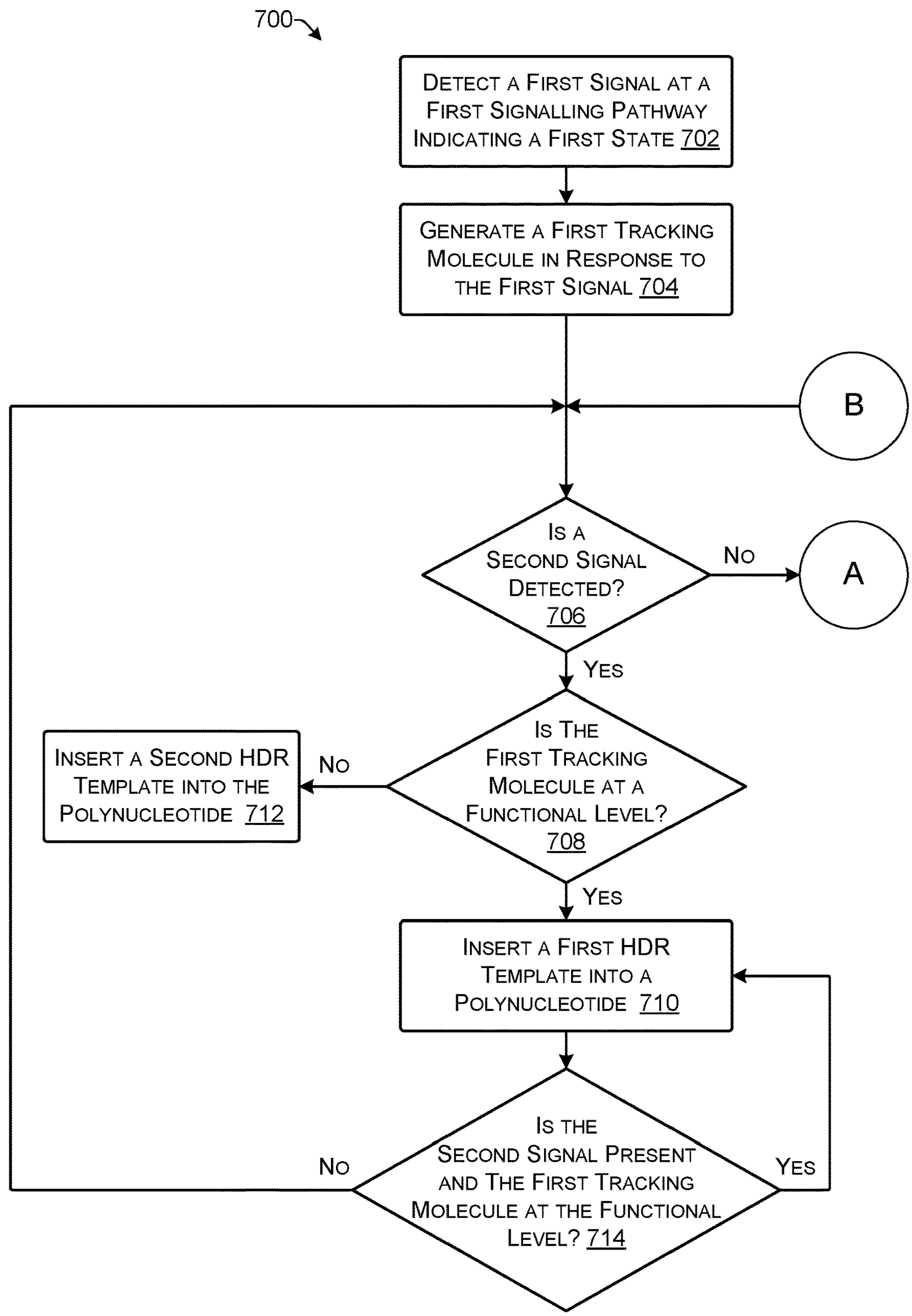
FIG. 7 shows an illustrative process for changing which HDR template is inserted in a double-stranded polynucleotide according to a state of a cell.

FIG. 7 shows a process 700 of controlling the HDR template that is inserted into a double-stranded polynucleotide based on the current state of a cell containing that double-stranded polynucleotide. Thus, the cell functions as a state machine in which the current state causes the cell to alter its behavior—specifically which HDR template that is inserted. As described above, setting the state may be done by the presence or absence of a chemical or chemical signal. Individual, distinct chemicals could be used to activate each of the discrete states of a cell. Alternatively, combinations of one or more chemicals may be used to activate a state. One way a state can be implemented is by affecting the behavior of a promoter. A promoter may be up regulated, down regulated, or silenced. The change in behavior of the promoter will affect the transcription of the gene or genes regulated by that promoter. The availability of the gene products may change which HDR templates are available for insertion, which locations have DSBs created, and which enzymes are available.

At 702, a first signal is detected at a first engineered signaling pathway. The first signal indicates a first state. The first engineered signaling pathway may be the same or similar as the engineered signaling pathway 502 shown in FIG. 5. The first signal and the first state may be the same or similar to first signal 406 and the $1^{st}$ state 402 shown in FIG. 4. The first signal may be an external signal that is detected by a membrane protein of the cell, an internal signal including a signal based on a natural process such as the cell cycle, or an internal signal based a detected condition that is detected internally without a membrane protein been present in the signal transduction pathway.

At 704, a first tracking molecule is generated in response to the first signal. The first tracking molecule may be the same or similar to the tracking molecule 504 shown in FIG. 5. In an implementation, the first tracking molecule can be a transcription factor that activates an inducible promoter. Inducible promoter may be operatively linked to at least one of synthesis of an HDR template or synthesis of a nuclease. Activation of the first tracking molecule in response to the first signal puts the cell into a first state. The first tracking molecule may decay below a functional level necessary to maintain the first state within a threshold time. The threshold time may be known based on understanding of known principles regarding the cellular system and the first tracking molecule. The threshold time may also be experimentally determined for a given cellular system and tracking molecule.

Figure 8:
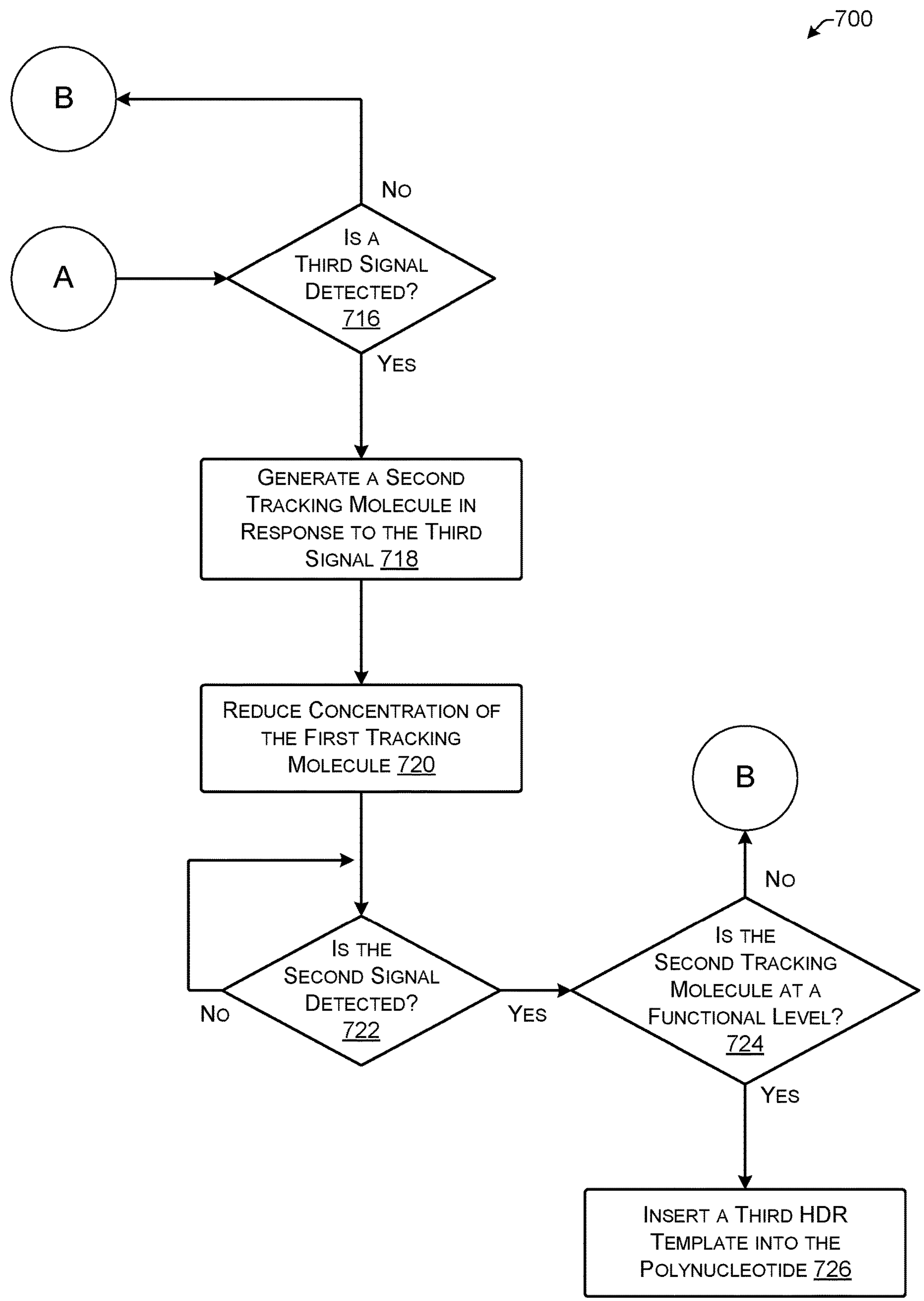
FIG. 8 is a continuation of the illustrative process of FIG. 7.

At 706, it is determined if a second signal is detected. The second signal may be representative of a sensed condition of the cell. For example, the second signal may indicate a condition in an environment surrounding the cell or a condition in the cell's internal environment. The cell may be configured to create a log of the second signal in a polynucleotide. If a second signal is not detected, then process 700 proceeds along the "no" path which is shown in FIG. 8 described below. If the second signal is detected, process 700 proceeds along the "yes" path.

At 708, it is determined if the first tracking molecule is at a functional level. If the first tracking molecule is at the functional level, then the cell is in the first state. If the first tracking molecule is below the functional level, then the cell is not in the first state. It may be in a second state, third state, undefined state, etc. The state of the cell controls which HDR template is inserted into a double-stranded polynucleotide as shown in FIG. 4. If the first tracking molecule is at or above the functional level, then process 700 proceeds along the "yes" path.

At 710, following the "yes" path, a first HDR template is inserted into the double-stranded polynucleotide in the cell. Insertion of this first HDR template indicates that the cell detected the second signal while in the first state. If however, at 708 the first tracking molecule was below the functional level, then process 700 proceeds along the "no" path.

At 712, following the "no" path a second HDR template is inserted into the double-stranded polynucleotide. Insertion of this HDR template indicates that the cell detected the second signal when the cell was not in the first state.

At 714, it is determined if the second signal is still present and the first tracking molecule is still at or above the functional level. If both are true, then the conditions are present at 710 still exist. In some implementations, the cell may iteratively insert the first HDR template while the second signal is present and the concentration of the first tracking molecule is at or above the functional level. In this situation, process 700 follows the "yes" path and returns to 710. Back at 710, a second copy of the first HDR template is again inserted into the double-stranded polynucleotide. As described above, this iterative insertion of the first HDR template may occur because the middle portion of the first HDR template includes a target site into which a further copy of the HDR template may be inserted.

If the second signal is no longer present or the first tracking molecule has dropped below the functional level, then process 700 proceeds along the "no" path from 714 and returns to 706. Thus, the cell is waiting until the second signal is again detected indicating a molecular to be logged. As described below, the cell may also respond to the detection of another signal different from the second signal (e.g. the second signal may correspond to light levels and another signal may correspond to temperature). If the second signal is not detected at 706, then process 700 proceeds along the "no" path shown in FIG. 8. FIG. 8 is a continuation of process 700.

At 716, it is determined if a third signal is detected at a second engineered signaling pathway. The third signal indicates a second state different from the first state. The third signal described here may be the same or similar as the second signal 408 shown in FIG. 4. The second state may be the same or similar to the 2$^{nd}$ state 404 shown in FIG. 4. The third signal may be any of the same types of molecules, environmental conditions, or signals as the first signal. However, the third signal is not the same as the first signal. If the third signal is not detected, then process 700 proceeds along the "no" path and returns to 706 shown on FIG. 7. Thus, when the cell is in the first state (or any state) the cell may wait for a second signal indicating a molecular signal which the cell logs in its genetic material or wait for a different kind of signal that transitions the cell to another state. If the third signal is detected, process 700 follows the "yes" path to 718.

At 718, a second tracking molecule is generated in response to the third signal. The second tracking molecule may be any of the same types of molecules as the first tracking molecule; however, it will be a different molecule so that the second state can be distinguished from the first state. Presence of the second tracking molecule in the cell at a level greater than a second threshold level places the cell in the second state.

At 720, as part of placing the cell in the second state, a concentration of the first tracking molecule is reduced. The concentration of the first tracking molecules may be reduced by repressing or silencing genes that cause synthesis of the first tracking molecules. Alternatively, the concentration of the first tracking molecule can be reduced by increasing expression of a protein that degrades the first tracking molecule. The protein may be a protease if the first tracking molecule is itself a protein or a nuclease if the first tracking molecule is a polynucleotide. Reducing the concentration of the first tracking molecule may be implemented by the inhibition system 536 shown in FIG. 5.

At 722, is determined if the second signal is detected. The second signal detected at 722 is the same as the second signal detected at 706. This is a signal representing a condition that the cell will log in a double-stranded polynucleotide if the condition is present. If the second signal is not detected, process 700 follows the "no" path and the cell may wait until the second signal is detected before modifying any polynucleotides. In response to detecting the second signal, process 700 follows "yes" path to 724.

At 724, is determined if a concentration of the second tracking molecule is at or above a second functional level. Because the first tracking molecule and the second tracking molecule are different molecules and may even be different types of molecules as well as potentially having different mechanisms of action, the first functional level the second functional level may represent different concentrations. If the second tracking molecule is at or above the second functional level then the cell is in the second state and process 700 proceeds along the "yes" path.

At 726, following the "yes" path, a third HDR template is inserted into the double-stranded polynucleotide. This third HDR template is different than the first HDR template or the second HDR template. Thus, even though the second signal is the same signal detected by the cell, being in the second state causes the cell to insert a different nucleotide sequence (i.e., the third HDR template) into the double-stranded polynucleotide.

If the second tracking molecule is below the second functional level, for example because the concentration of the second tracking molecule decreased with time, then process 700 proceeds along the "no" path and returns to 706 on FIG. 7 waiting for the second signal or another signal that will place the cell into a different state.

Illustrative System and Computing Devices

Figure 9:
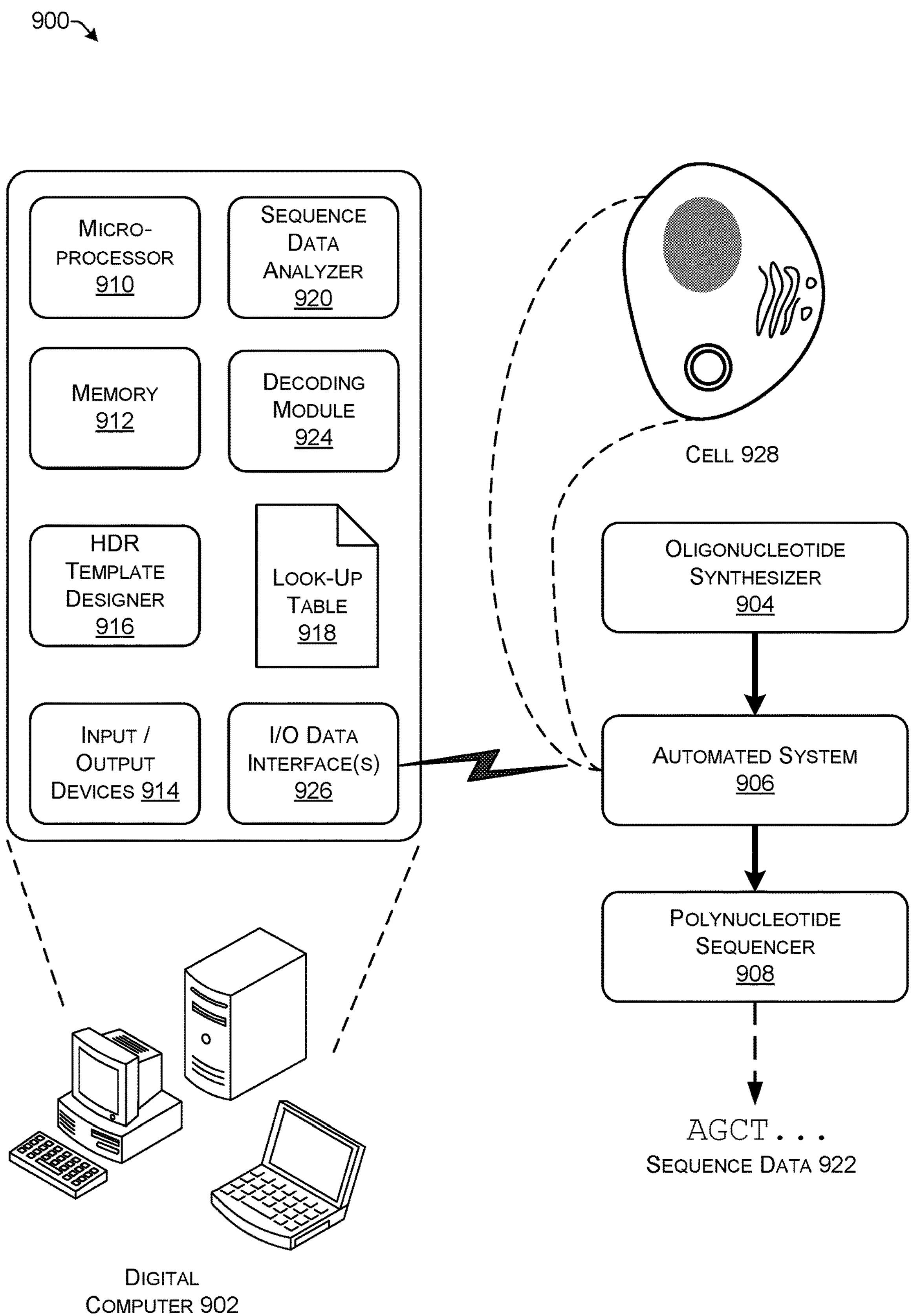
FIG. 9 shows an illustrative system for implementing the techniques described in this disclosure.

FIG. 9 shows an illustrative architecture 900 for implementing and interacting with DNA molecules recording logs and arbitrary information by use of HDR as described above. The architecture may include any of a digital computer 902, an oligonucleotide synthesizer 904, an automated system 906, and/or a polynucleotide sequencer 908. The architecture 900 may also include other components besides those discussed herein.

As used herein, "digital computer" means a computing device including at least one hardware microprocessor 910 and memory 912 capable of storing information in a binary format. The digital computer 902 may be a supercomputer, a server, a desktop computer, a notebook computer, a tablet computer, a game console, a mobile computer, a smartphone, or the like. The hardware microprocessor 910 may be implemented in any suitable type of processor such as a single core processor, a multicore processor, a central processing unit (CPU), a graphical processing unit (GPU), or the like. The memory 912 may include removable storage, non-removable storage, local storage, and/or remote storage to provide storage of computer readable instructions, data structures, program modules, and other data. The memory 912 may be implemented as computer-readable media. Computer-readable media includes, at least, two types of media, namely computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer readable instructions, data structures, program modules, or other data in a modulated data signal, such as a carrier wave, or other transmission mechanism. As defined herein, computer-readable storage media and communications media are mutually exclusive.

The digital computer 902 may also include one or more input/output devices(s) 914 such as a keyboard, a pointing device, a touchscreen, a microphone, a camera, a display, a speaker, a printer, and the like.

An HDR template designer 916 may be included as part of the digital computer 902, for example, as instructions stored in the memory 912. The HDR template designer 916 may design HDR templates based on sequences of target sites, sequences of dsDNA molecules, enzyme recognition sites, etc. In one implementation, the HDR template designer 916 may design HDR templates to avoid cross talk between different signal recording pathways. The HDR template designer 916 may also compare percent similarity and hybridization conditions for potential HDR templates as well as portions of the HDR templates. For example, the HDR template designer 916 may design HDR templates to avoid the formation of hairpins as well as to prevent or minimize annealing between HDR templates. The HDR template designer 916 may also design HDR templates to maximize a difference between the 3'-end sequence, 5'-end sequence, and/or middle sequence. For example, the difference may be G:C content and the HDR template designer 916 may design sequences with a preference for increasing the G:C content difference between the end sequences and the middle sequence.

The digital computer 902 may also include a look-up table 918. However, the look-up table 918 may be part of a hardware device that is physically separate from the digital computer 902. The look-up table 918 includes the correspondence between the sequence of an HDR template and a meaning such as signal (e.g., GGTACA means exposure to bright light) or arbitrary information such as a binary digit (e.g., AAC followed by GAT means "1"). For example, the information that expression of a given HDR template is up regulated in the presence of a given signal is one example of a correspondence that may be stored in the look-up table 918. The look-up table 918 may store any number of different associations between signals/timing indicators and HDR templates. The look-up table 918 may be pre-calculated and stored in static program storage, calculated (or "pre-fetched") as part of a program's initialization phase (e.g., memorization), or even stored in hardware in an application-specific platform.

A sequence data analyzer 920 may analyze sequence data 922 generated by the polynucleotide sequencer 908. The sequence data analyzer 920 may be implemented as instructions stored in the memory 912. Thus, sequence data 922 may be provided to the sequence data analyzer 920 which analyzes the sequence data 922 at least in part by comparison to nucleotide sequences contained in the look-up table 918.

A decoding module 924 may decode the sequence data 922 in order to identify a sequence of binary digits or other arbitrary information stored in the sequence data 922. A list of the sequences of possible HDR templates and the order of those templates that encode a particular binary digit can be stored in decoding module 924, so that the decoding module 924 can implement the context-dependent code. Thus, the sequence data 922 may be passed from the sequence data analyzer 920 to decoding module 924 where the series of A, G, C, and Ts is converted into a string of binary digits. Alternatively, the sequence data 922 may go directly from the polynucleotide sequencer 908 to the decoding module 924 without prior processing by the sequence data analyzer 920.

In order to manipulate the DNA and potentially RNA that makes up the HDR templates and dsDNA, the digital computer 902 may communicate with other devices through one or more I/O data interfaces 926. The I/O data interface (s) 926 can exchange instructions and data with other devices such as the oligonucleotide synthesizer 904, the automated system 906, and the polynucleotide sequencer 908.

The oligonucleotide synthesizer 904 chemically synthesizes oligonucleotides based on instructions received as electronic data. The synthesized oligonucleotides may be used as HDR templates, as dsDNA molecules that provide target sites, as plasmids, vectors, or other components. Thus, in some implementations, the sequence of nucleotides which is provided to the oligonucleotide synthesizer 904 may come from the HDR template designer 916.

A number of methods for DNA synthesis and commercial oligonucleotide synthesizers are available. Methods for DNA synthesis include solid-phase phosphoramidite synthesis, microchip-based oligonucleotide synthesis, ligation-mediated assembly, PCR-mediated assembly, and the like. For example, such synthesis can be performed using an ABI 394 DNA Synthesizer (Applied Biosystems, Foster City, Calif.). One having ordinary skill in the art can use an oligonucleotide synthesizer to create desired nucleotides.

The term "oligonucleotide" as used herein is defined as a molecule including two or more nucleotides. Oligonucleotides include probes and primers. Oligonucleotides used as probes or primers may also include nucleotide analogues such as phosphorothioates, alkylphosphorothioates, peptide nucleic acids, or intercalating agents. The introduction of these modifications may be advantageous in order to positively influence characteristics such as hybridization kinetics, reversibility of the hybrid-formation, stability of the oligonucleotide molecules, and the like.

The automated system 906 may include any type of robotics, automation, or other system for automating one or more manipulations that may be performed on the dsDNA with the enzymes and/or the HDR templates. The automated system 906 may be used in conjunction with manual operations such that the totality of operations needed to be performed to practice the techniques of this disclosure are done so in a hybrid manner in which some are performed by the automated system 906 and others manually.

In one implementation, the automated system 906 may include a microfluidics system. An illustrative microfluidics system may be configured to move small volumes of liquid according to techniques well-understood by those of ordinary skill in the art. As used herein, the automated system 906 may include other equipment for manipulating DNA beyond that expressly shown in FIG. 9 such as, for example, a thermocycler.

The automated system 906 may include a cell-free system that can be implemented in part by microfluidics. The cell-free system may also be implemented as an artificial cell or a minimal cell. As used herein the term "cell" encompasses natural cells 928, artificial cells, and minimal cells unless context clearly indicates otherwise. The natural cells 928 may be prokaryotic cells or eukaryotic cells. A prokaryotic cell may comprise a cell envelope and a cytoplasmic region that contains the cell genome (DNA) and ribosomes and various sorts of inclusions. In some embodiments, the cells are bacterial cells. As used herein, the term "bacteria" encompasses all variants of bacteria, for example, prokaryotic organisms and cyanobacteria. A eukaryotic cell comprises membrane-bound compartments in which specific metabolic activities take place, such as a nucleus. Examples of eukaryotic cells include, without limitation, mammalian cells, insect cells, yeast cells (e.g., *S. cerevisiae*) and plant cells. In some embodiments, the eukaryotic cells are from a vertebrate animal. Examples of vertebrate cells for use in accordance with the invention include, without limitation, reproductive cells including sperm, ova and embryonic cells, and non-reproductive cells, including kidney, lung, spleen, lymphoid, cardiac, gastric, intestinal, pancreatic, muscle, bone, neural, brain and epithelial cells. Stem cells, including embryonic stem cells, can also be used.

One or more natural cells 928 may be present as cells in culture. Some human cell lines that may be used for cell culture include DU145, H295R, HeLa, KBM-7, LNCaP, MCF-7, MDA-MB-468, PC3, SaOS-2, SH-SY5Y, T47D, THP-1, U87, and National Cancer Institute's 60 cancer cell line panel (NCI60). A culture of cells in the automated system 906 may be manipulated by an automated cell culture system. Natural cells 928 may also be present outside of the automated system 906. An artificial cell or minimal cell is an engineered particle that mimics one or many functions of a biological cell. Artificial cells are biological or polymeric membranes which enclose biologically active materials. As such, nanoparticles, liposomes, polymersomes, microcapsules, detergent micelles, and a number of other particles may be considered artificial cells. Microencapsulation allows for metabolism within the membrane, exchange of small molecules and prevention of passage of large substances across it. Membranes for artificial cells can be made of simple polymers, crosslinked proteins, lipid membranes or polymer-lipid complexes. Further, membranes can be engineered to present surface proteins such as albumin, antigens, Na/K-ATPase carriers, or pores such as ion channels. Commonly used materials for the production of membranes include hydrogel polymers such as alginate, cellulose and thermoplastic polymers such as hydroxyethyl methacrylate-methyl methacrylate (HEMA-MMA), polyacrylonitrile-polyvinyl chloride (PAN-PVC), as well as variations of the above-mentioned materials.

Minimal cells, also known as proto-cells, are cells that help all the minimum requirements for life. Minimal cells may be created by a top-down approach that knocks out genes in a single-celled organism until a minimal set of genes necessary for life are identified. *Mycoplasma mycoides, E. coli*, and *S. cerevisiae*, are examples of organisms that may be modified to create minimal cells. One of ordinary skill in the art will recognize multiple techniques for generating minimal cells.

The cell-free system includes components for DNA replication and repair such as nucleotides, DNA polymerase, and DNA ligase. The cell-free system will also include dsDNA that includes at least one initial target site for creating a DSB. The dsDNA may be present in the vector that includes one or more operons. The cell-free system will also include buffers to maintain pH and ion availability. Furthermore, the cell-free system may also include the enzymes used for creating DSBs in dsDNA and the HDR templates used for repairing dsDNA. Some cell-free systems may include genes encoding the enzymes and HDR templates. To prevent enzymes from remaining when their respective cutting functions are no longer desired, the cell-free system may include proteolytic enzymes that specifically break down nucleases.

In a cell-free system, particular components may be added when needed either by moving volumes of liquid together with microfluidics or by increasing the expression of gene products that leads to synthesis of enzymes, HDR templates, etc.

The automated system 906 may include a structure, such as at least one chamber, which holds one or more DNA molecules. The chamber may be implemented as any type of mechanical, biological, or chemical arrangement which holds a volume of liquid, including DNA, to a physical location. For example, a single flat surface having a droplet present thereon, with the droplet held by surface tension of the liquid, even though not fully enclosed within a container, is one implementation of a chamber.

The automated system 906 may perform many types of manipulations on DNA molecules. For example, the automated system 906 may be configured to move a volume of liquid from one chamber to another chamber in response to a series of instructions from the I/O data interface 926.

The polynucleotide sequencer 908 may sequence DNA molecules using any technique for sequencing polynucleotides known to those skilled in the art including classic dideoxy sequencing reactions (Sanger method), sequencing by synthesis using reversibly terminated labeled nucleotides, pyrosequencing, nanopore sequencing, SOLiD sequencing, chemical-sensitive field effect transistor (chemFET) sequencing, and ion semiconductor sequencing. The polynucleotide sequencer 908 may be configured to sequence all or part of a dsDNA molecule modified according to any of the techniques described above and provide the sequence data 922 to the digital computer 902.

Any natural cells 928 present may be prepared for sequencing by extracting nucleic acids according to standard methods in the art. For example, DNA from a cell can be isolated using various lytic enzymes, chemical solutions, or extracted by nucleic acid binding resins following instructions provided by a manufacturer. DNA contained in extracted sample may be detected by amplification procedures such as PCR or hybridization assays according to methods widely known in the art.

The sequence data 922 generated by sequencing can be sent from the polynucleotide sequencer 908 to the digital computer 902 for analysis by the sequence data analyzer 920, the decoding module 924, and also for presentation on an output device 914.

Illustrative Site-Specific Nucleases

Restriction enzymes (restriction endonucleases) are present in many species and are capable of sequence-specific binding to DNA (at a target or recognition site), and cleaving DNA at or near the site of binding. Over 3000 restriction enzymes have been studied in detail, and more than 600 of these are available commercially. Naturally occurring restriction endonucleases are categorized into four groups (Types I, II III, and IV) based on their composition and enzyme cofactor requirements, the nature of their target site, and the position of their DNA cleavage site relative to the target site. All types of enzymes recognize specific short DNA sequences and carry out the endonucleolytic cleavage of DNA to give specific fragments with terminal 5'-phosphates. One type of restriction enzyme, Type II enzymes, cleave within or at short specific distances from a recognition site; most require magnesium; single function (restriction) enzymes independent of methylase. Type II enzymes form homodimers, with recognition sites that are usually undivided and palindromic and 4-8 nt in length. They recognize and cleave DNA at the same site, and they do not use ATP or AdoMet for their activity—they usually require only Mg' as a cofactor. Common type II restriction enzymes include HhaI, HindIII, NotI, EcoRI, and BglI. Restriction enzymes may cut dsDNA in a way that leaves either blunt ends or sticky ends. Protocols for creating a DSB in dsDNA with restriction enzymes are well known to those skilled in the art. Restriction digest is a common molecular biology technique and is typically performed using the reagents and protocols provided in a commercially available restriction digest kit. Examples of companies that provide restriction digest kits include New England BioLabs, Promega, Sigma-Aldrich, and Thermo Fisher Scientific. Each of these companies provides restriction digest protocols on their website.

Homing endonucleases (HEs), which are also known as meganucleases, are a collection of double-stranded DNases that have large, asymmetric recognition sites (12-40 nt) and coding sequences that are usually embedded in either introns or inteins. Introns are spliced out of precursor RNAs, while inteins are spliced out of precursor proteins. They catalyze the hydrolysis of genomic DNA within the cells that synthesize them, but do so at few, or even a single, location(s) per genome. HE recognition sites are extremely rare. For example, an 18 nt recognition sequence will occur only once in every $7\times10^{10}$ nt of random sequence. This is equivalent to only one site in 20 mammalian-sized genomes. However, unlike restriction endonucleases, HEs tolerate some sequence degeneracy within their recognition sequence. Thus, single base changes do not abolish cleavage but reduce its efficiency to variable extents. As a result, their observed sequence specificity is typically in the range of 10-12 nt. Examples of suitable protocols using HEs may be found in Flick, K. et al., *DNA Binding in Cleavage by the Nuclear Introns Encoded Homing Endonuclease I-Ppol,* 394 Nature 96 (1998) and Chevalier, B. et al., *Design, Activity, and Structure of a Highly Specific Artificial Endonuclease,* 10 Molecular Cell 895 (2002).

Zinc finger nucleases (ZFNs) are synthetic proteins consisting of an engineered zinc finger DNA-binding domain fused to the cleavage domain of the FokI restriction endonuclease. ZFNs can be used to induce DSBs in specific DNA sequences and thereby promote site-specific homologous recombination and targeted manipulation of genomic loci in a variety of different cell types. The introduction of a DSB into dsDNA may enhance the efficiency of recombination with an exogenously introduced HDR template. ZFNs consist of a DNA-binding zinc finger domain (composed of three to six fingers) covalently linked to the non-specific DNA cleavage domain of the bacterial FokI restriction endonuclease. ZFNs can bind as dimers to their target DNA sites, with each monomer using its zinc finger domain to recognize a half-site. Dimerization of ZFNs is mediated by the FokI cleavage domain which cleaves within a five or six nucleotide "spacer" sequence that separates the two inverted "half sites." Because the DNA-binding specificities of zinc finger domains can in principle be re-engineered using one of various methods, customized ZFNs can be constructed to target nearly any DNA sequence. One of ordinary skill in the art will know how to design and use ZFNs to create DSBs in dsDNA at a desired target site. Some suitable protocols are available in Philipsborn, A. et al., *Microcontact printing of axon guidance molecules for generation of graded patterns,* 1 Nature Protocols 1322 (2006); John Young and Richard Harland, *Targeted Gene Disruption with Engineered Zinc Finger Nucleases* (*ZFNs*), 917 Xenopus Protocols 129 (2012), and Hansen, K. et al. *Genome Editing with CompoZr Custom Zinc Finger Nucleases* (*ZFNs*), 64 J. Vis. Exp. 3304 (2012).

TALENs are restriction enzymes that can be engineered to cut specific sequences of DNA. They are made by fusing a TAL effector DNA-binding domain to a DNA cleavage domain (i.e., a nuclease which cuts DNA strands). Transcription activator-like effectors (TALEs) can be engineered to bind practically any desired DNA sequence, so when combined with a nuclease, DNA can be cut at specific locations. The restriction enzymes can be introduced into cells, for use in gene editing or for genome editing in situ. The DNA binding domain contains a repeated highly conserved 33-34 amino acid sequence with divergent $12^{th}$ and $13^{th}$ amino acids. These two positions, referred to as the Repeat Variable Diresidue (RVD), are highly variable and show a strong correlation with specific nucleotide recognition. This straightforward relationship between amino acid sequence and DNA recognition has allowed for the engineering of specific DNA-binding domains by selecting a combination of repeat segments containing the appropriate RVDs. Notably, slight changes in the RVD and the incorporation of "nonconventional" RVD sequences can improve targeting specificity. One of ordinary skill in the art will know how to design and use TALENs to create DSBs in dsDNA at a desired target site. Some suitable protocols are available in Hermann, M. et al., *Mouse Genome Engineering Using Designer Nucleases,* 86 J. Vis. Exp. 50930 (2014) and Sakuma, T. et al., *Efficient TALEN Construction and Evaluation Methods for Human Cell and Animal Applications,* 18(4) Genes Cells 315 (2013).

In the CRISPR/Cas nuclease system, the CRISPR locus, encodes RNA components of the system, and the Cas (CRISPR-associated) locus, encodes proteins. CRISPR loci in microbial hosts contain a combination of CRISPR-associated (Cas) genes as well as non-coding RNA elements capable of programming the specificity of the CRISPR-mediated polynucleotide cleavage.

The Type II CRISPR is one of the most well characterized systems and carries out targeted DSBs in four sequential steps. First, two non-coding RNAs, the pre-crRNA array and tracrRNA, are transcribed from the CRISPR locus. A "crRNA" is a bacterial RNA that confers target specificity and requires tracrRNA to bind to Cas9. A "tracrRNA" is a bacterial RNA that links the crRNA to the Cas9 nuclease and typically can bind any crRNA. Second, tracrRNA hybridizes to the repeat regions of the pre-crRNA and mediates the processing of pre-crRNA into mature crRNAs containing individual spacer sequences. Third, the mature crRNA:

tracrRNA complex directs Cas9 to the target DNA via Watson-Crick base-pairing between the spacer on the crRNA and the protospacer on the target DNA next to the protospacer adjacent motif (PAM), an additional requirement for target recognition. In engineered CRISPR/Cas9 systems, gRNA also called single-guide RNA ("sgRNA") may replace crRNA and tracrRNA with a single RNA construct that includes the protospacer element and a linker loop sequence. A gRNA refers to a fusion of a CRISPR-targeting RNA (crRNA) and a trans-activation crRNA (tracrRNA), providing both targeting specificity and scaffolding/binding ability for Cas9 nuclease. The sequence specificity of a Cas DNA-binding protein is determined by gRNAs, which have nucleotide base-pairing complementarity to target DNA sequences. Thus, Cas proteins are "guided" by gRNAs to target DNA sequences. The nucleotide base-pairing complementarity of gRNAs enables, in some embodiments, simple and flexible programming of Cas binding. Nucleotide base-pair complementarity refers to distinct interactions between adenine and thymine (DNA) or uracil (RNA), and between guanine and cytosine. In some embodiments, a gRNA is referred to as a stgRNA. A "stgRNA" is a gRNA that complexes with Cas9 and guides the stgRNA/Cas9 complex to the template DNA from which the stgRNA was transcribed.

The length of a gRNA may vary. In some embodiments, a gRNA has a length of 20 to 200 nt, or more. For example, a gRNA may have a length of 20 to 175, 20 to 150, 20 to 100, 20 to 95, 20 to 90, 20 to 85, 20 to 80, 20 to 75, 20 to 70, 20 to 65, 20 to 60, 20 to 55, 20 to 50, 20 to 45, 20 to 40, 20 to 35, or 20 to 30 nt.

Standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). In the context of this disclosure, a guanine (G) is considered complementary to a uracil (U), and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary. Use of gRNA may simplify the components needed to use CRISPR/Cas9 for genome editing. The Cas9 species of different organisms have different PAM sequences. For example, *Streptococcus pyogenes* (Sp) has a PAM sequence of 5'-NGG-3', *Staphylococcus aureus* (Sa) has a PAM sequence of 5'-NGRRT-3' or 5'-NGRRN-3', *Neisseria meningitidis* (NM) has a PAM sequence of 5'-NNNNGATT-3', *Streptococcus thermophilus* (St) has a PAM sequence of 5'-NNAGAAW-3', *Treponema denticola* (Td) has a PAM sequence of 5'-NAAAAC-3'.

Finally, Cas9 mediates cleavage of target DNA to create a DSB within the protospacer. Activity of the CRISPR/Cas system in nature comprises three steps: (i) insertion of alien DNA sequences into the CRISPR array to prevent future attacks, in a process called "adaptation," (ii) expression of the relevant proteins, as well as expression and processing of the array, followed by (iii) RNA-mediated interference with the alien polynucleotide. The alien polynucleotides come from viruses attaching the bacterial cell. Thus, in the bacterial cell, several of the so-called 'Cas' proteins are involved with the natural function of the CRISPR/Cas system and serve roles in functions such as insertion of the alien DNA, etc.

CRISPR may also function with nucleases other than Cas9. Two genes from the Cpf1 family contain a RuvC-like endonuclease domain, but they lack Cas9's second HNH endonuclease domain. Cpf1 cleaves DNA in a staggered pattern and requires only one RNA rather than the two (tracrRNA and crRNA) needed by Cas9 for cleavage. Cpf1's preferred PAM is 5'-TTN, differing from that of Cas9 (3'-NGG) in both genomic location and GC-content. Mature crRNAs for Cpf1-mediated cleavage are 42-44 nt in length, about the same size as Cas9's, but with the direct repeat preceding the spacer rather than following it. The Cpf1 crRNA is also much simpler in structure than Cas9's; only a short stem-loop structure in the direct repeat region is necessary for cleavage of a target. Cpf1 also does not require an additional tracrRNA. Whereas Cas9 generates blunt ends 3 nt upstream of the PAM site, Cpf1 cleaves in a staggered fashion, creating a five nucleotide 5' overhang 18-23 nt away from the PAM.

Other known or later discovered CRISPR-associated proteins besides Cas9 may be used instead of Cas9. For example, CRISPR-associated protein 1 (Cas1) is one of the two universally conserved proteins found in the CRISPR prokaryotic immune defense system. Cas1 is a metal-dependent DNA-specific endonuclease that produces double-stranded DNA fragments. Cas1 forms a stable complex with the other universally conserved CRISPR-associated protein, Cas2, which is part of spacer acquisition for CRISPR systems. Other Cas enzymes include Cas3, CasX, and CasY as described in Burstein, et al., *New CRISPR-Cas systems from uncultivated microbes.* 542 Nature 237 (2017).

There are also CRISPR/Cas9 variants that do not use a PAM sequence such as NgAgo. NgAgo functions with a 24-nucleotide ssDNA guide and is believed to cut 8-11 nt from the start of this sequence. The ssDNA is loaded as the protein folds and cannot be swapped to a different guide unless the temperature is increased to non-physiological 55° C. A few nucleotides in the target DNA are removed near the cut site. Techniques for using NgAgo are described in Gao, F. et al., *DNA-guided Genome Editing Using the Natronobacterium Gregoryi Argonaute,* 34 Nature Biotechnology 768 (2016).

DSBs may be formed by making two single-stranded breaks at different locations creating a cut DNA molecule with sticky ends. Single-strand breaks or "nicks" may be formed by modified versions of the Cas9 enzyme containing only one active catalytic domain (called "Cas9 nickase"). Cas9 nickases still bind DNA based on gRNA specificity, but nickases are only capable of cutting one of the DNA strands. Two nickases targeting opposite strands are required to generate a DSB within the target DNA (often referred to as a "double nick" or "dual nickase" CRISPR system). This requirement dramatically increases target specificity, since it is unlikely that two off-target nicks will be generated within close enough proximity to cause a DSB. Techniques for using a dual nickase CRISPR system to create a DSB are described in Ran, et al., *Double Nicking by RNA-Guided CRISPR Cas9* for Enhanced Genome Editing Specificity, 154 Cell 6:1380 (2013).

In certain embodiments, any of the enzymes described in this disclosure may be a "functional derivative" of a naturally occurring protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of an enzyme or a fragment thereof include but are not limited to mutants, fusions, covalent modifications of the protein or a fragment thereof. The enzyme, or a fragment thereof, as well as derivatives or a fragment thereof, may be obtainable from a cell or synthesized chemically or by a combination of these two procedures. The cell may be a cell that naturally produces the enzyme. A cell that naturally produces enzyme may also be genetically engineered to produce the endogenous enzyme at a higher expression level or to produce the enzyme from an exogenously introduced polynucleotide, which polynucleotide encodes an enzyme that is the same or different from the endogenous enzyme. In some cases, a cell does not naturally produce the enzyme and is genetically engineered to produce the enzyme. The engineering may include adding the polynucleotide encoding the enzyme under the control of a promoter. The promoter may be an inducible promoter that is activated in response to a signal. The promoter may also be blocked by a different signal or molecule.

Illustrative Promoters

As used herein, a "promoter" is a DNA regulatory region capable of binding RNA polymerase and initiating transcription of a downstream (3' direction) coding or non-coding sequence. Promoters are located near the transcription start sites of genes, on the same strand and upstream on the DNA (towards the 5' region of the sense strand). A promoter sequence is bounded at its 3' terminus by the transcription initiation site and extends upstream (5'direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention. A promoter may also contain sub-regions at which regulatory proteins and molecules may bind, such as RNA polymerase and other transcription factors. Promoters may be constitutive, inducible, activatable, repressible, tissue-specific or any combination thereof. Illustrative promoters are described below.

Promoters described in this disclosure may include any promoter known in the art for expression either in vivo or in vitro. Promoters may include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). The promoters may also be inducible, such that expression may be decreased or enhanced or turned "on" or "off." For example, promoters which respond to a particular signal (e.g., small molecule, metabolite, protein, molecular modification, ion concentration change, electric charge change, action potential, radiation, UV, and light) may also be used. Additionally, a tetracycline-regulatable system employing any promoter such as, but not limited to, the U6 promoter or the H1 promoter, may be used. By way of example and not of limitation, promoters which respond to a particular stimulus may include, e.g., heat shock protein promoters, and Tet-off and Tet-on promoters.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

A promoter drives expression or drives transcription of the nucleic acid sequence that it regulates. The term "operably linked" as used herein means placing a gene under the regulatory control of a promoter, which then controls the transcriptional initiation or expression of that sequence and optionally the translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

A promoter may be one naturally associated with a gene or sequence, as may be obtained by isolating the 5' non-coding sequences located upstream of the coding segment of a given gene or sequence. Such a promoter is referred to as an "endogenous promoter."

In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR). Contemplated herein, in some embodiments, are RNA pol II and RNA pol III promoters. Promoters that direct accurate initiation of transcription by an RNA polymerase II are referred to as RNA pol II promoters. Examples of RNA pol II promoters for use in accordance with the present disclosure include, without limitation, human cytomegalovirus promoters, human ubiquitin promoters, human histone H2A1 promoters and human inflammatory chemokine CXCL 1 promoters. Other RNA pol II promoters are also contemplated herein. Promoters that direct accurate initiation of transcription by an RNA polymerase III are referred to as RNA pol III promoters. Examples of RNA pol III promoters for use in accordance with the present disclosure include, without limitation, a U6 promoter, a HI promoter and promoters of transfer RNAs, 5S ribosomal RNA (rRNA), and the signal recognition particle 7SL RNA.

Illustrative promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31 (17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

"Constitutive promoters" are typically active, i.e., promote transcription, under most conditions. "Inducible promoters" are typically active only under certain conditions, such as in the presence of a given molecule factor (e.g., IPTG) or a given environmental condition (e.g., particular $CO_2$ concentration, nutrient levels, light, heat). In the absence of that condition, inducible promoters typically do not allow significant or measurable levels of transcriptional activity. For example, inducible promoters may be induced according to temperature, pH, a hormone, a metabolite (e.g., lactose, mannitol, an amino acid), light (e.g., wavelength specific), osmotic potential (e.g., salt induced), a heavy metal, or an antibiotic. Numerous standard inducible promoters are known to one of skill in the art.

Illustrative eukaryotic promoters known to one of skill in the art are listed below.

| Promoter | Primarily used for | Description | Additional considerations |
|---|---|---|---|
| CMV | General expression | Strong mammalian expression promoter from the human cytomegalovirus | May contain an enhancer region. Can be silenced in some cell types. |
| EF1a | General expression | Strong mammalian expression from human elongation factor 1 alpha | Tends to give consistent expression regardless of cell type or physiology. |
| SV40 | General expression | Mammalian expression promoter from the simian vacuolating virus 40 | May include an enhancer. |
| PGK1 (human or mouse) | General expression | Mammalian promoter from phosphoglycerate kinase gene. | Widespread expression, but may vary by cell type. Tends to resist promoter down regulation due to methylation or deacetylation. |
| Ubc | General expression | Mammalian promoter from the human ubiquitin C gene | As the name implies, this promoter is ubiquitous. |
| human beta actin | General expression | Mammalian promoter from beta actin gene | Ubiquitous. Chicken version is commonly used in promoter hybrids. |
| CAG | General expression | Strong hybrid mammalian promoter | Contains CMV enhancer, chicken beta actin promoter, and rabbit beta-globin splice acceptor. |
| TRE | General expression | Tetracycline response element promoter | Typically contains a minimal promoter with low basal activity and several tetracycline operators. Transcription can be turned on or off depending on what tet transactivator is used. |
| UAS | General expression | *Drosophila* promoter containing Gal4 binding sites | Requires the presence of Gal4 gene to activate promoter. |
| Ac5 | General expression | Strong insect promoter from *Drosophila* Actin 5c gene | Commonly used in expression systems for *Drosophila*. |
| Polyhedrin | General expression | Strong insect promoter from baculovirus | Commonly used in expression systems for insect cells. |
| CaMKIIa | Gene expression for optogenetics | Ca2+/calmodulin-dependent protein kinase II promoter | Used for neuronal/CNS expression. Modulated by calcium and calmodulin. |
| GAL1, 10 | General expression | Yeast adjacent, divergently transcribed promoters | Can be used independently or together. Regulated by GAL4 and GAL 80. |
| TEF1 | General expression | Yeast transcription elongation factor promoter | Analogous to mammalian EF1a promoter. |

-continued

| Promoter | Primarily used for | Description | Additional considerations |
|---|---|---|---|
| GDS | General expression | Strong yeast expression promoter from glyceraldehyde 3-phosphage dehydrogenase | Very strong, also called TDH3 or GAPDH. |
| ADH1 | General expression | Yeast promoter for alcohol dehydrogenase I | Full-length version is strong with high expression. Truncated promoters are constitutive with lower expression. |
| CaMV35S | General expression | Strong plant promoter from the Cauliflower Mosaic Virus | Active in dicots, less active in monocots, with some activity in animal cells. |
| Ubi | General expression | Plant promoter from maize ubiquitin gene | Gives high expression in plants. |
| H1 | small RNA expression | From the human polymerase III RNA promoter | May have slightly lower expression than U6. May have better expression in neuronal cells. |
| U6 | small RNA expression | From the human U6 small nuclear promoter | Murine U6 is also used, but may be less efficient. |

Illustrative prokaryotic promoters known to one of skill in the art are listed below.

| Promoter | Primarily used for | Description | Expression | Additional considerations |
|---|---|---|---|---|
| T7 | in vitro transcription/ general expression | Promoter from T7 bacteriophage | Constitutive, but requires T7 RNA polymerase. | When used for in vitro transcription, the promoter drives either the sense OR antisense transcript depending on its orientation to your gene. |
| T7lac | High levels of gene expression | Promoter from T7 bacteriophage plus lac operators | Negligible basal expression when not induced. Requires T7 RNA polymerase, which is also controlled by lac operator. Can be induced by IPTG. | Commonly found in pET vectors. Very tightly regulated by the lac operators. Good for modulating gene expression through varied inducer concentrations. |
| Sp6 | in vitro transcription/ general expression | Promoter from Sp6 bacteriophage | Constitutive, but requires SP6 RNA polymerase. | SP6 polymerase has a high processivity. When used for in vitro transcription, the promoter drives either the sense OR antisense transcript depending on its orientation to your gene. |
| araBAD | General expression | Promoter of the arabinose metabolic operon | Inducible by arabinose and repressed catabolite repression in the presence of glucose or by competitive binding of the anti-inducer fucose | Weaker. Commonly found in pBAD vectors. Good for rapid regulation and low basal expression; however, not well-suited for modulating gene expression through varied inducer concentrations. |
| trp | High levels of gene expression | Promoter from *E. coli* tryptophan operon | Repressible | Gets turned off with high levels of cellular tryptophan. |
| lac | General expression | Promoter from lac operon | Constitutive in the absence of lac repressor (lacI or lacIq). Can be induced by IPTG or lactose. | Leaky promoter with somewhat weak expression. lacIq mutation increases expression of the repressor 10x, thus tightening regulation of lac promoter. Good for modulating gene expression through varied inducer concentrations. |

-continued

| Promoter | Primarily used for | Description | Expression | Additional considerations |
|---|---|---|---|---|
| Ptac | General expression | Hybrid promoter of lac and trp | Regulated like the lac promoter | Contains −35 region from trpB and −10 region from lac. Very tight regulation. Good for modulating gene expression through varied inducer concentrations. Generally better expression than lac alone. |
| pL | High levels of gene expression | Promoter from bacteriophage lambda | Can be temperature regulatable | Often paired with the temperature sensitive c1857 repressor. |

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document, "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A molecular state machine implemented in a cell comprising: an engineered signaling pathway that generates a tracking molecule in response to a first signal associated with a first state; an operon that changes a rate of transcription of an RNA product based on the tracking molecule; a double-stranded polynucleotide having a target site; a homology directed repair (HDR) template with homology to the target site, wherein an amount of the HDR template available in the cell or an activity of a nuclease configured to create a double strand break (DSB) at a cut site in the target site is increased by the RNA product; and an inhibition system that reduces the amount of HDR template available in the cell or the activity of the nuclease.

Clause 2. The molecular state machine of clause 1, wherein the tracking molecule is a transcription factor.

Clause 3. The molecular state machine of clause 1 or 2, wherein the RNA product is mRNA that encodes the nuclease.

Clause 4. The molecular state machine of any of clauses 1-3, wherein the RNA product is a gRNA and the nuclease is a CRISPR-associated protein.

Clause 5. The molecular state machine of any of clauses 1-4, wherein the RNA product is the HDR template or is a template for generating the HDR template through reverse transcription.

Clause 6. The molecular state machine of any of clauses 1-5, wherein the inhibition system responds to a second signal associated with a second state.

Clause 7. The molecular state machine of clause 6, wherein the inhibition system comprises CRISPRi that inactivates the operon.

Clause 8. A method of encoding binary data in a polynucleotide within a cell, the method comprising: receiving a first external signal that indicates a first binary digit; inserting a first HDR template into a double stranded polynucleotide by HDR, the first HDR template representative of the first binary digit according to a context-dependent code; generating a first molecular signal based on the first binary digit, presence of the first molecular signal placing the cell into a first state; receiving a second external signal that indicates a second binary digit; and inserting a second HDR template into the double-stranded polynucleotide by HDR, the second HDR template representative of the second binary digit according to the context-dependent code and based on the cell being in the first state.

Clause 9. The method of clause 8, wherein the first molecular signal comprises a transcription factor that activates a promoter associated with the first state of the cell.

Clause 10. The method of clause 8 or 9, wherein the second HDR template comprises a 3'-end sequence and a 5'-end sequence that are homologous to corresponding portions of a target site on the double-stranded polynucleotide, and a middle region that comprises an identifier region that represents the second binary digit and an additional target site having a sequence based on the first state.

Clause 11. The method of any of clauses 8-10, wherein the context-dependent code prevents adjacent insertions of a same polynucleotide sequence into the double-stranded polynucleotide.

Clause 12. The method of clauses 8-11, further comprising: generating a second molecular signal based on the second binary digit, presence of the second molecular signal placing the cell into a second state different than the first state; receiving a third external signal that indicates a third binary digit; and inserting a third HDR template into the double-stranded polynucleotide by HDR, the third HDR template representative of the third binary digit according to the context-dependent code and based on the cell being in the second state.

Clause 13. The method of clause 12, wherein the first state is a first stable state of a bi-stable molecular switch and the second state is a second state of the bi-stable molecular switch.

Clause 14. A method for recording a signal in a cell based on state, the method comprising: detecting a first signal at a first engineered signaling pathway indicating a first state; generating a first tracking molecule in response to the first signal; detecting a second signal; and responsive to the second signal and when a concentration of the first tracking molecule is at or above a first functional level, inserting a first HDR template into a double-stranded polynucleotide in the cell.

Clause 15. The method of clause 14, wherein the first tracking molecule is a transcription factor that activates an inducible promoter operatively linked to at least one of synthesis of the HDR template or synthesis of a nuclease that creates a double strand break (DSB) in the double-stranded polynucleotide.

Clause 16. The method of clause 14 or 15, wherein the concentration of the first tracking molecule decays below the first functional level within a threshold time.

Clause 17. The method of clause 16, further comprising responsive to the second signal and when the concentration of the first tracking molecule is below the first functional level, inserting a second HDR template into the double-stranded polynucleotide.

Clause 18. The method of any of clauses 14-17, further comprising iteratively inserting the first HDR template while the second signal is present and the concentration of the first tracking molecule is at or above the first functional level.

Clause 19. The method of any of clauses 14-18, further comprising: detecting a third signal at a second engineered signaling pathway indicating a second state different from the first state; generating a second tracking molecule in response to the third signal; reducing the concentration of the first tracking molecule in response to the third signal; detecting the second signal; and responsive to the second signal and when a concentration of the second tracking molecule is at or above a second functional level, inserting a third HDR template into the double-stranded polynucleotide.

Clause 20. The method of clause 19, wherein the reducing the concentration of the first tracking molecule causes increasing expression of a protein that degrades the first tracking molecule.

CONCLUSION

The terms “a,” “an,” “the” and similar referents used in the context of describing the invention (especially in the context of the following claims) are to be construed to cover both the singular and the plural, unless otherwise indicated herein or clearly contradicted by context. The term “based on” is to be construed to cover both exclusive and nonexclusive relationships. For example, “A is based on B” means that A is based at least in part on B and may be based wholly on B. By “about” is meant a quantity, level, value, number, frequency, percentage, dimension, size, amount, weight, or length that varies by as much as 10, 9, 8, 7, 6, 5, 4, 3, 2 or 1% to a reference quantity, level, value, number, frequency, percentage, dimension, size, amount, weight, or length.

All methods described herein can be performed in any suitable order unless otherwise indicated herein or otherwise clearly contradicted by context. The use of all examples and exemplary language (e.g., “such as”) provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

Furthermore, references have been made to publications, patents and/or patent applications (collectively “references”) throughout this specification. Each of the cited references is individually incorporated herein by reference for its particular cited teachings as well as for all that it discloses.

The invention claimed is:

1. A molecular state machine implemented in a cell and comprising:

an RNA product in the cell;

an engineered signaling pathway in the cell that is configured to generate a tracking molecule in response to a first signal associated with a first state;

an operon in the cell that is configured to change a rate of transcription of the RNA product based on the tracking molecule;

a double-stranded polynucleotide in the cell having a target site;

a nuclease in the cell configured to create a double strand break (DSB) at a cut site in the target site;

a homology directed repair (HDR) template in the cell with homology to the target site, wherein the RNA product is configured to increase an amount of the HDR template available in the cell or an activity of the nuclease configured to create the DSB at the cut site in the target site; and a regulatory element in the cell that is configured to reduce the amount of HDR template available in the cell or the activity of the nuclease.

2. The molecular state machine of claim 1, wherein the tracking molecule is a transcription factor.

3. The molecular state machine of claim 1, wherein the RNA product is mRNA that encodes the nuclease.

4. The molecular state machine of claim 1, wherein the RNA product is a gRNA and the nuclease is a CRISPR associated protein.

5. The molecular state machine of claim 1, wherein the RNA product is the HDR template or is a template configured for generating the HDR template through reverse transcription.

6. The molecular state machine of claim 1, wherein the regulatory element is configured to reduce the amount of HDR template available in the cell or the activity of the nuclease in response to a second signal associated with a second state.

7. The molecular state machine of claim 6, wherein the regulatory element comprises a repressor protein, a silencer, mRNA, or catalytically inactive Cas9 lacking endonuclease activity.

8. A method of using a molecular state machine within a cell, the method comprising:

receiving a first signal associated with a first state, wherein an engineered signaling pathway of the cell generates a tracking molecule in response to the first signal;

changing, by an operon of the cell and based on the tracking molecule, the rate of transcription of an RNA product in the cell;

creating, by nuclease in the cell, a double strand break (DSB) at a cut site in a target site of a double-stranded polynucleotide;

increasing, in the cell, the amount of a homology directed repair (HDR) template with homology to the target site available in the cell or the activity of the nuclease configured to create the DSB at the cut site in the target site, wherein the increasing is based on availability of the RNA product; and reducing, by a regulatory element in the cell, the amount of HDR template available in the cell or the activity of the nuclease.

9. The method of claim 8, wherein the wherein the tracking molecule is a transcription factor.

10. The method of claim 8, wherein the RNA product is mRNA that encodes the nuclease.

11. The method of claim 8, wherein the RNA product is a gRNA and the nuclease is a CRISPR-associated protein.

12. The method of claim 8, wherein the RNA product is the HDR template or is a template configured for generating the HDR template through reverse transcription.

13. The method of claim 8 further comprising, receiving a second signal associated with a second state, wherein the second signal activates the inhibition system.

* * * * *

SEQUENCE LISTING

```
<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: X1 example

<400> SEQUENCE: 1

tagccgtatc gagcatcgat g                                               21


<210> SEQ ID NO 2
<211> LENGTH: 11
<212> TYPE: DNA
<213> ORGANISM: Artificial Sequence
```

```
<220> FEATURE:
<223> OTHER INFORMATION: X2 example
<220> FEATURE:
<221> NAME/KEY: misc_feature
<222> LOCATION: (4)..(7)
<223> OTHER INFORMATION: n is a, c, g, or t

<400> SEQUENCE: 2

cgcnnnngat t                                                             11


<210> SEQ ID NO 3
<211> LENGTH: 21
<212> TYPE: DNA
<213> ORGANISM: Artificial Sequence
<220> FEATURE:
<223> OTHER INFORMATION: Y1 example

<400> SEQUENCE: 3

gatcgatgga ctctgcatct a                                                  21


<210> SEQ ID NO 4
<211> LENGTH: 11
<212> TYPE: DNA
<213> ORGANISM: Artificial Sequence
<220> FEATURE:
<223> OTHER INFORMATION: Y2 example
<220> FEATURE:
<221> NAME/KEY: misc_feature
<222> LOCATION: (4)..(7)
<223> OTHER INFORMATION: n is a, c, g, or t

<400> SEQUENCE: 4

tcgnnnngat t                                                             11


<210> SEQ ID NO 5
<211> LENGTH: 21
<212> TYPE: DNA
<213> ORGANISM: Artificial Sequence
<220> FEATURE:
<223> OTHER INFORMATION: Z1 example

<400> SEQUENCE: 5

cgggacgatc gatcgggcta g                                                  21


<210> SEQ ID NO 6
<211> LENGTH: 11
<212> TYPE: DNA
<213> ORGANISM: Artificial Sequence
<220> FEATURE:
<223> OTHER INFORMATION: Z2 example
<220> FEATURE:
<221> NAME/KEY: misc_feature
<222> LOCATION: (4)..(7)
<223> OTHER INFORMATION: n is a, c, g, or t

<400> SEQUENCE: 6

actnnnngat t                                                             11


<210> SEQ ID NO 7
<211> LENGTH: 64
<212> TYPE: DNA
<213> ORGANISM: Artificial Sequence
<220> FEATURE:
<223> OTHER INFORMATION: Homology directed repair sequences of X1Y1Y2X2
<220> FEATURE:
<221> NAME/KEY: misc_feature
<222> LOCATION: (46)..(49)
<223> OTHER INFORMATION: n is a, c, g, or t
<220> FEATURE:
```

```
<221> NAME/KEY: misc_feature
<222> LOCATION: (57)..(60)
<223> OTHER INFORMATION: n is a, c, g, or t

<400> SEQUENCE: 7

tagccgtatc gagcatcgat ggatcgatgg actctgcatc tatcgnnnng attcgcnnnn     60

gatt                                                                  64


<210> SEQ ID NO 8
<211> LENGTH: 64
<212> TYPE: DNA
<213> ORGANISM: Artificial Sequence
<220> FEATURE:
<223> OTHER INFORMATION: Homology directed repair sequences Y1X1X2Y2
<220> FEATURE:
<221> NAME/KEY: misc_feature
<222> LOCATION: (46)..(49)
<223> OTHER INFORMATION: n is a, c, g, or t
<220> FEATURE:
<221> NAME/KEY: misc_feature
<222> LOCATION: (57)..(60)
<223> OTHER INFORMATION: n is a, c, g, or t

<400> SEQUENCE: 8

gatcgatgga ctctgcatct atagccgtat cgagcatcga tgcgcnnnng atttcgnnnn     60

gatt                                                                  64


<210> SEQ ID NO 9
<211> LENGTH: 12
<212> TYPE: DNA
<213> ORGANISM: Artificial Sequence
<220> FEATURE:
<223> OTHER INFORMATION: Repeated subsequence in target sequence example

<400> SEQUENCE: 9

gtactagtac ta                                                         12
```